US009775574B2

(12) United States Patent
Jones et al.

(10) Patent No.: US 9,775,574 B2
(45) Date of Patent: Oct. 3, 2017

(54) XRF ANALYZER

(71) Applicant: Moxtek, Inc., Orem, UT (US)

(72) Inventors: Vincent Floyd Jones, Cedar Hills, UT (US); Daniel N. Paas, Spanish Fork, UT (US)

(73) Assignee: Moxtek, Inc., Orem, UT (US)

( * ) Notice: Subject to any disclaimer, the term of this patent is extended or adjusted under 35 U.S.C. 154(b) by 383 days.

(21) Appl. No.: 14/615,134

(22) Filed: Feb. 5, 2015

(65) Prior Publication Data

US 2015/0308968 A1 Oct. 29, 2015

Related U.S. Application Data

(60) Provisional application No. 61/985,163, filed on Apr. 28, 2014.

(51) Int. Cl.
*H01J 35/16* (2006.01)
*H01J 37/16* (2006.01)
(Continued)

(52) U.S. Cl.
CPC ............ *A61B 6/4405* (2013.01); *A61B 6/107* (2013.01); *A61B 6/4429* (2013.01);
(Continued)

(58) Field of Classification Search
CPC .. A61B 6/00; A61B 6/10; A61B 6/107; A61B 6/40; A61B 6/44; A61B 6/4405; A61B 6/4411; A61B 6/4429; A61B 6/46; A61B 6/467; A61B 6/48; A61B 6/485; A61B 6/54; A61B 2560/00; A61B 2560/04; A61B 2560/0406; A61B 2560/0425; A61B 2560/0431; A61B 2560/0443; A61B 2560/0462; A61B 2560/0487; H01J 5/00; H01J 5/02; H01J 5/04; H01J 5/08; H01J 5/18; H01J 5/48; H01J 5/50; H01J 5/54; H01J 9/24; H01J 9/26; H01J 9/28; H01J 9/30; H01J 9/34; H01J 9/36; H01J 9/40; H01J 35/00; H01J 35/02; H01J 35/025; H01J 35/16; H01J 37/00; H01J 37/02; H01J 37/16; H01J 37/165; H01J 2235/00; H01J 2235/16; H01J 2235/163; H01J 2235/165; H01J 2235/166; H01J 2235/18;
(Continued)

(56) References Cited

U.S. PATENT DOCUMENTS 7,020,238 B1    3/2006  Kantonen et al.
7,375,359 B1 *  5/2008  Grodzins ............. G01N 23/223
                                                    250/515.1
(Continued)

FOREIGN PATENT DOCUMENTS

EP           1686369 B1    12/2010
KR    10-2008-0098103 A    11/2008
(Continued)

*Primary Examiner* — Anastasia Midkiff
(74) *Attorney, Agent, or Firm* — Thorpe, North & Western, LLP

(57) ABSTRACT

A portable XRF analyzer includes a hand shield to substantially block x-rays from impinging on a hand of a user. The portable XRF analyzer includes a heat sink over an x-ray source and a heat sink over an x-ray detector. The heat sinks are separated from each other by a thermally insulative material.

21 Claims, 24 Drawing Sheets

(51) Int. Cl.

| | |
|---|---|
| *H05G 1/04* | (2006.01) |
| *H05G 1/02* | (2006.01) |
| *G01N 23/223* | (2006.01) |
| *G21F 5/02* | (2006.01) |
| *G21F 5/04* | (2006.01) |
| *G21F 5/06* | (2006.01) |
| *A61B 6/00* | (2006.01) |
| *A61B 6/10* | (2006.01) |
| *G21F 1/10* | (2006.01) |
| *H05G 1/06* | (2006.01) |
| *G21F 5/015* | (2006.01) |
| *H01J 5/50* | (2006.01) |
| *H01J 5/04* | (2006.01) |
| *H01J 9/36* | (2006.01) |
| *H01J 35/02* | (2006.01) |

(52) U.S. Cl.
CPC ........... *G01N 23/223* (2013.01); *G21F 1/106* (2013.01); *G21F 5/015* (2013.01); *G21F 5/02* (2013.01); *G21F 5/04* (2013.01); *G21F 5/06* (2013.01); *H01J 35/16* (2013.01); *H01J 37/165* (2013.01); *H05G 1/04* (2013.01); *H05G 1/06* (2013.01); *A61B 6/485* (2013.01); *A61B 2560/0406* (2013.01); *A61B 2560/0425* (2013.01); *A61B 2560/0431* (2013.01); *A61B 2560/0462* (2013.01); *G01N 2223/076* (2013.01); *G01N 2223/301* (2013.01); *H01J 5/04* (2013.01); *H01J 5/50* (2013.01); *H01J 9/36* (2013.01); *H01J 35/025* (2013.01); *H01J 2235/16* (2013.01); *H01J 2235/163* (2013.01); *H01J 2235/165* (2013.01); *H01J 2235/166* (2013.01); *H01J 2237/0266* (2013.01)

(58) Field of Classification Search
CPC ............... H01J 2237/00; H01J 2237/02; H01J 2237/0203; H01J 2237/026; H01J 2237/0266; H01J 2237/06; H01J 2237/061; H01J 2237/16; H05G 1/00; H05G 1/02; H05G 1/04; H05G 1/06; G01N 23/00; G01N 23/22; G01N 23/223; G01N 2223/00; G01N 2223/07; G01N 2223/076; G01N 2223/10; G01N 2223/101; G01N 2223/1016; G01N 2223/20; G01N 2223/30; G01N 2223/301; G01N 2223/308; G01T 7/00; G21F 1/00; G21F 1/02; G21F 1/10; G21F 1/103; G21F 1/106; G21F 1/12; G21F 1/125; G21F 3/00; G21F 5/00; G21F 5/015; G21F 5/02; G21F 5/04; G21F 5/06
See application file for complete search history.

(56) References Cited

U.S. PATENT DOCUMENTS

| | | | | |
|---|---|---|---|---|
| 2006/0098779 | A1* | 5/2006 | Turner | A61B 6/14 378/102 |
| 2007/0230659 | A1 | 10/2007 | Turner | |
| 2009/0057582 | A1* | 3/2009 | Dugas | G01N 35/00732 250/522.1 |
| 2009/0129550 | A1* | 5/2009 | Bandy | H01J 1/135 378/141 |
| 2010/0226476 | A1* | 9/2010 | Pesce | G01N 23/223 378/44 |
| 2013/0003923 | A1 | 1/2013 | Sackett | |
| 2013/0156155 | A1 | 6/2013 | Hession-Kunz et al. | |
| 2014/0301533 | A1* | 10/2014 | Failla, Jr. | G01N 23/223 378/45 |

FOREIGN PATENT DOCUMENTS

| | | |
|---|---|---|
| WO | WO 2005/010514 A1 | 2/2005 |
| WO | WO 2015/167638 A1 | 11/2015 |

\* cited by examiner

XRF ANALYZER

PRIORITY CLAIM(S)

Priority is claims to U.S. Provisional Patent Application Ser. No. 61/985,163, filed Apr. 28, 2014; which is hereby incorporated herein by reference.

FIELD OF THE INVENTION

The present application is related generally to x-ray fluorescence (XRF) analyzers.

BACKGROUND

Aspects of an XRF analyzer can include (1) shielding a hand of a user from x-rays (emitted from an x-ray source in the analyzer or fluoresced from a sample); (2) removing heat from an x-ray detector, an x-ray source, or both in the XRF analyzer; and (3) thermally separating the x-ray detector from the x-ray source in order to avoid heat from the x-ray source adversely affecting resolution of the x-ray detector. Information relevant to attempts to address these problems can be found in U.S. Patent Publication Number US 2013/0003923 and European Patent Number EP 1,686,369.

SUMMARY

It has been recognized that it would be advantageous in an x-ray fluorescence (XRF) analyzer to: (1) shield the hand of the user from x-rays; (2) remove heat from the x-ray detector, the x-ray source, or both; and (3) thermally separate the x-ray detector from the x-ray source. The present invention is directed to various embodiments of a portable XRF analyzer and a method of assembling a portable XRF analyzer that satisfy these needs. Each embodiment may satisfy one, some, or all of these needs.

The XRF analyzer can comprise an engine component having an x-ray emission end. An x-ray source and an x-ray detector can be disposed in and substantially enclosed by the engine component. The x-ray source can be disposed in a location and oriented to emit x-rays outward from the x-ray emission end towards a sample. The x-ray detector can be disposed in a location and oriented to receive fluoresced x-rays emitted from the sample. A handle can extend from the engine component and can allow a user to hold and carry the XRF analyzer.

In one embodiment, a hand shield can extend from the engine component, parallel to the handle, and can be disposed closer to the x-ray emission end than the handle. There can be a finger-gap between the handle and the hand shield. A casing of the hand shield and a casing of the engine component can include a material for blocking x-rays.

In another embodiment, an x-ray source heat-sink can be disposed in an opening in a casing of the engine component and adjacent a side of the x-ray source, and an x-ray detector heat-sink can be disposed in another opening in the casing of the engine component and adjacent a side of the x-ray detector. The x-ray source heat-sink can be separated from the x-ray detector heat sink by a material having a low thermal conductivity.

A method of assembling a portable XRF analyzer can comprise injection molding an XRF analyzer housing in two separate portions and attaching the two XRF analyzer housing portions to each other. Each portion can include a an engine component casing section attached to a power component casing section by a handle casing section and a hand shield casing section. The handle casing section and the hand shield casing section can extend in two separate, parallel columns between the engine component casing section and the power component casing section. The two engine component casing sections can sandwich an x-ray source and an x-ray detector. The two hand shield casing sections can form a hand shield. The two handle casing sections can form a handle. The hand shield can be disposed closer to an x-ray emission end of the x-ray source than the handle.

DEFINITIONS

As used herein, "parallel" means, with regard to the handle and the hand shield extending parallel to each other, or the handle and the hand shield extending in parallel, that these two columnar-shaped structures extend side-by-side substantially in the same direction. Parallel does not necessarily mean that these two columns are equidistant from each other at all points.

DETAILED DESCRIPTION

Figure 5:
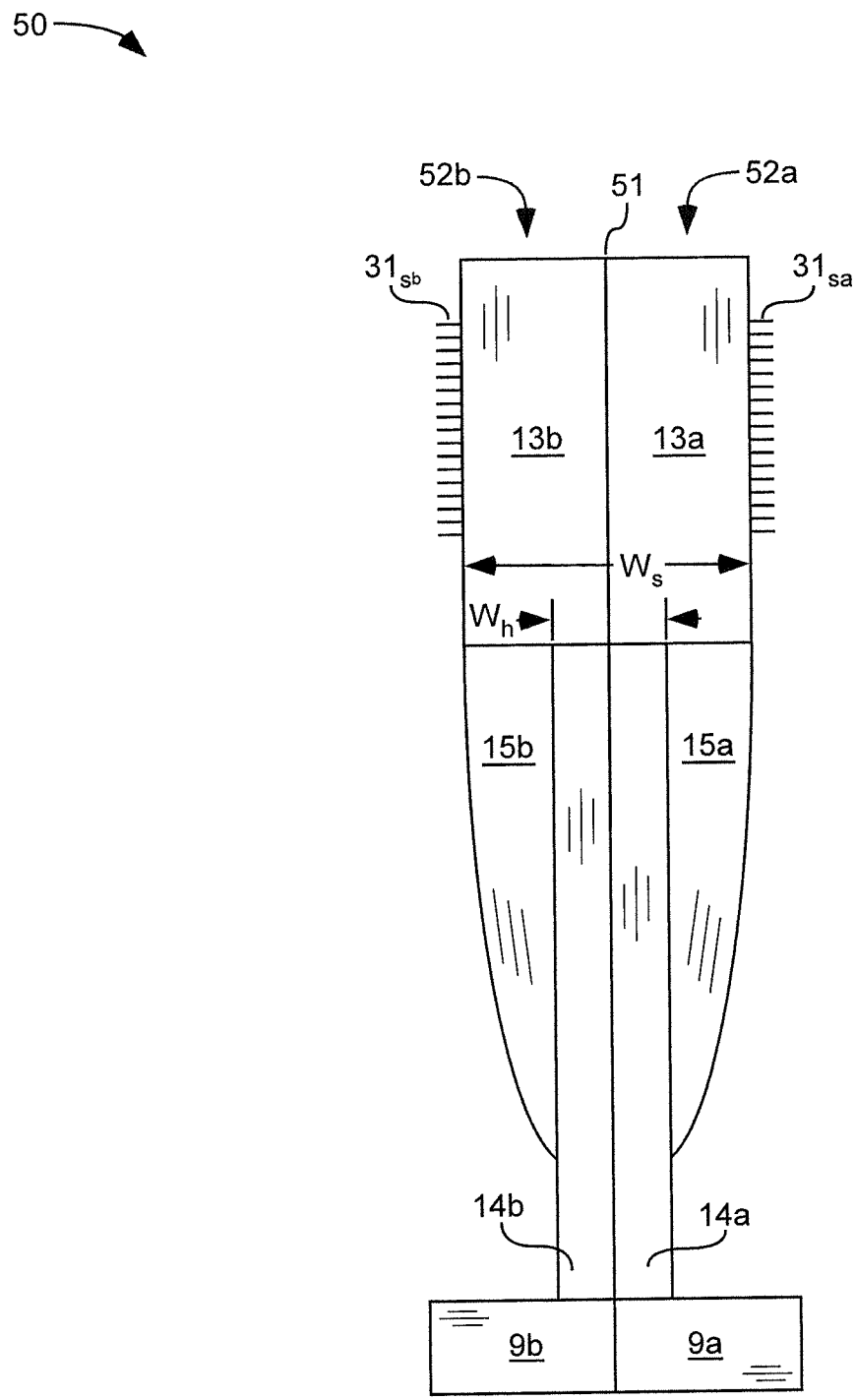
FIG. 5 is a schematic back view of an XRF analyzer, in accordance with an embodiment of the present invention.
Figure 6:
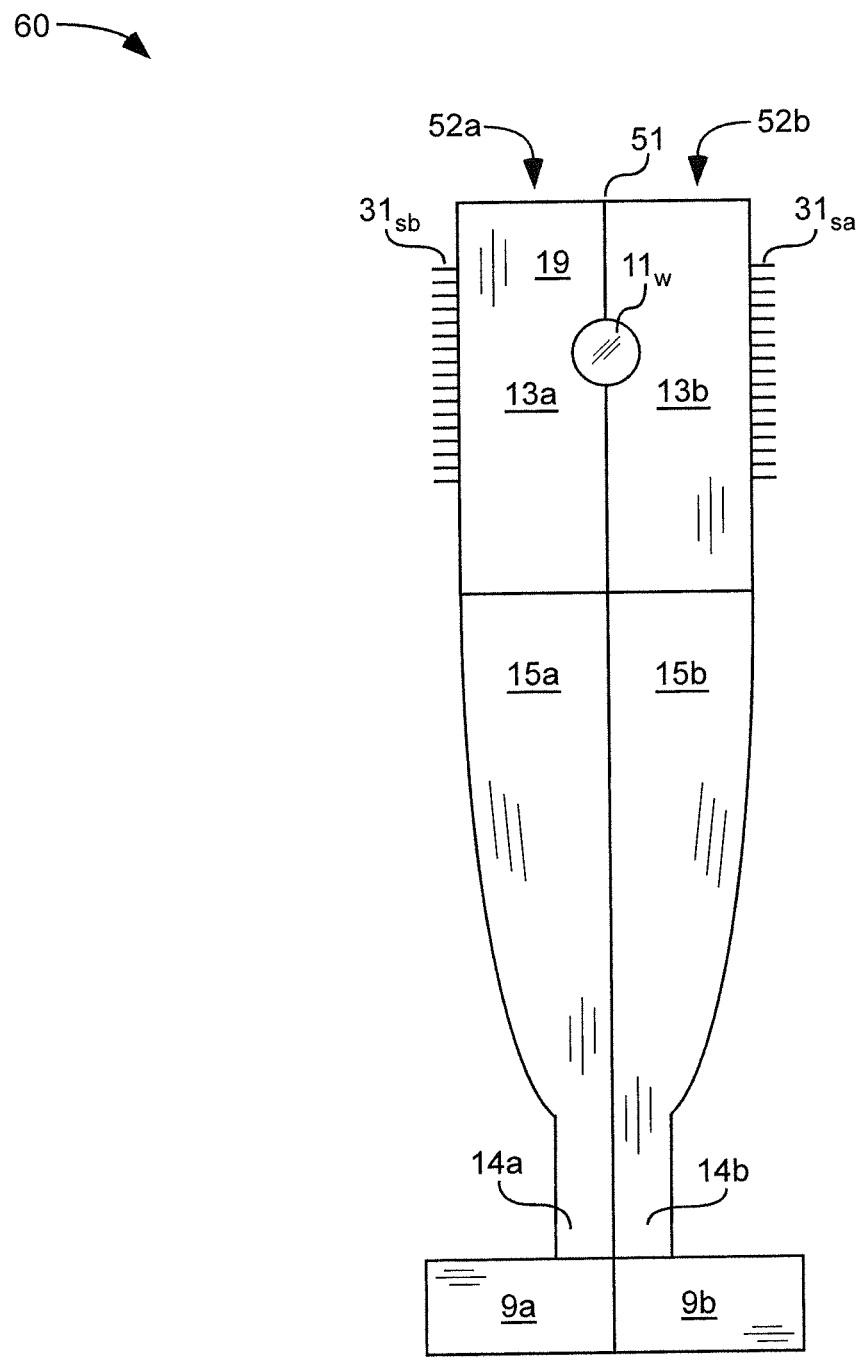
FIG. 6 is a schematic front view of an XRF analyzer, in accordance with an embodiment of the present invention.
Figure 13:
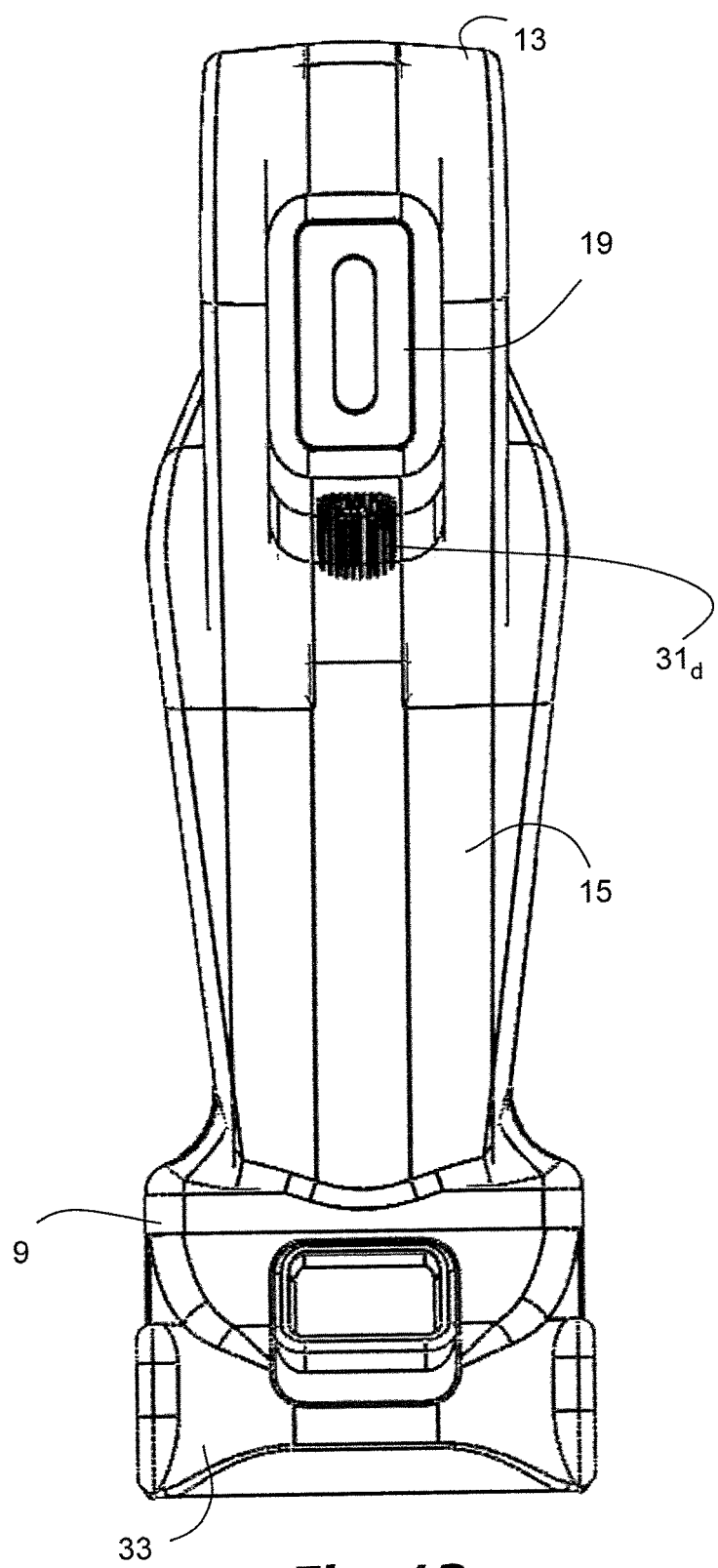
FIG. 13 is a schematic front view of an XRF analyzer with an attached battery, in accordance with an embodiment of the present invention.
Figure 14:
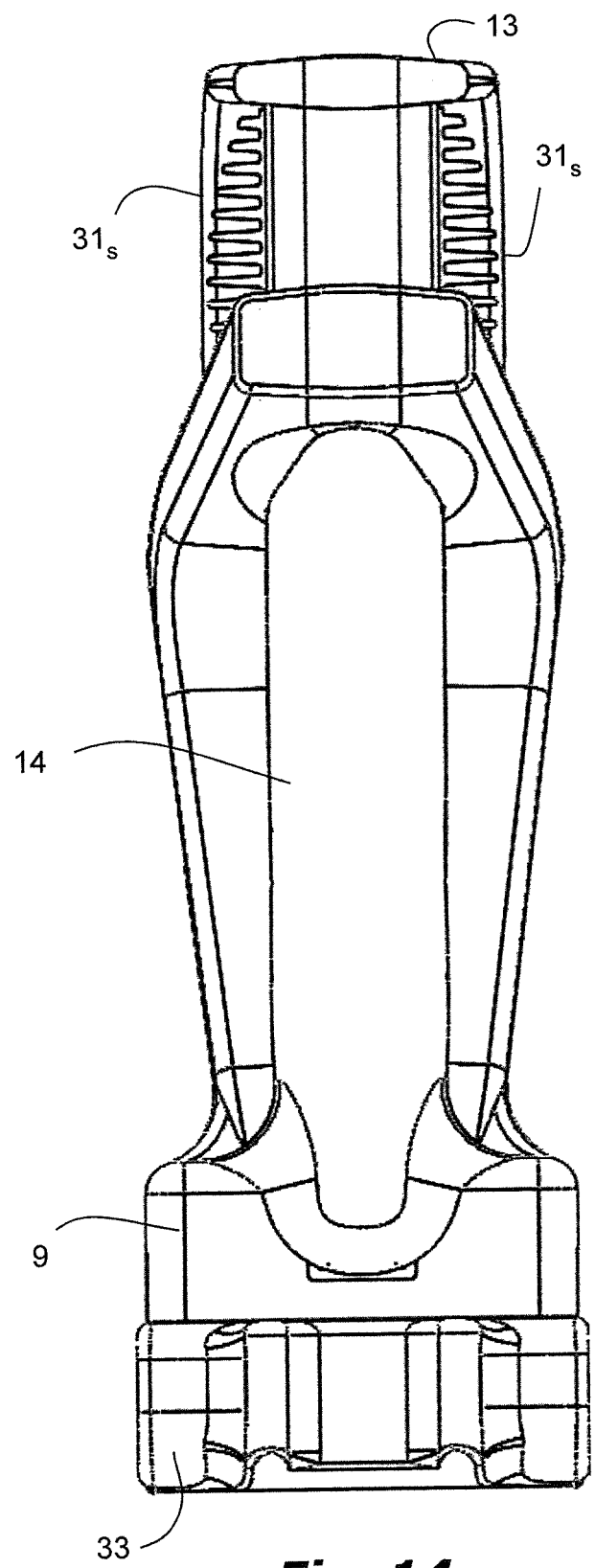
FIG. 14 is a schematic back view of an XRF analyzer with an attached battery, in accordance with an embodiment of the present invention.
Figure 15:
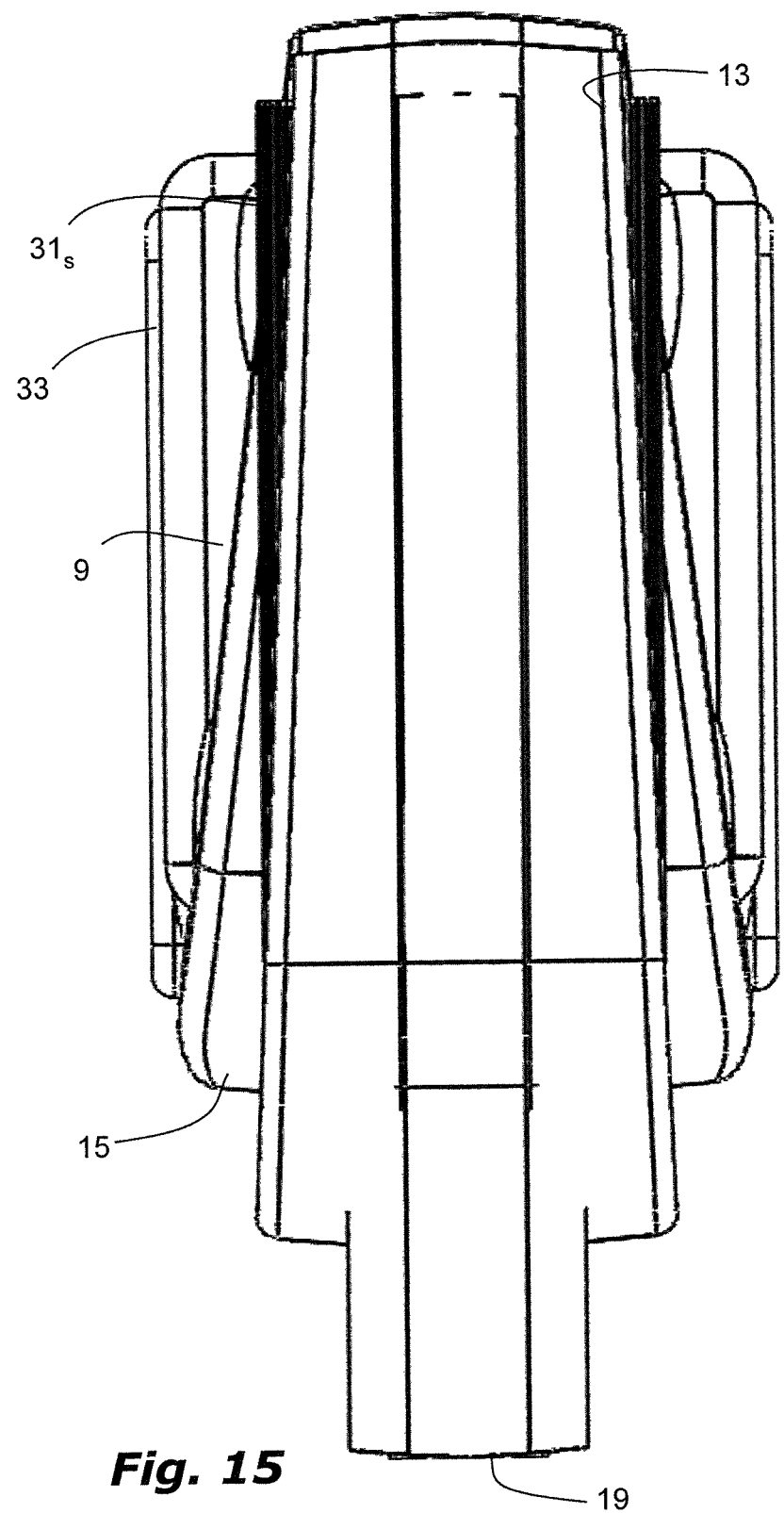
FIG. 15 is a schematic top view of an XRF analyzer with an attached battery, in accordance with an embodiment of the present invention.
Figure 16:
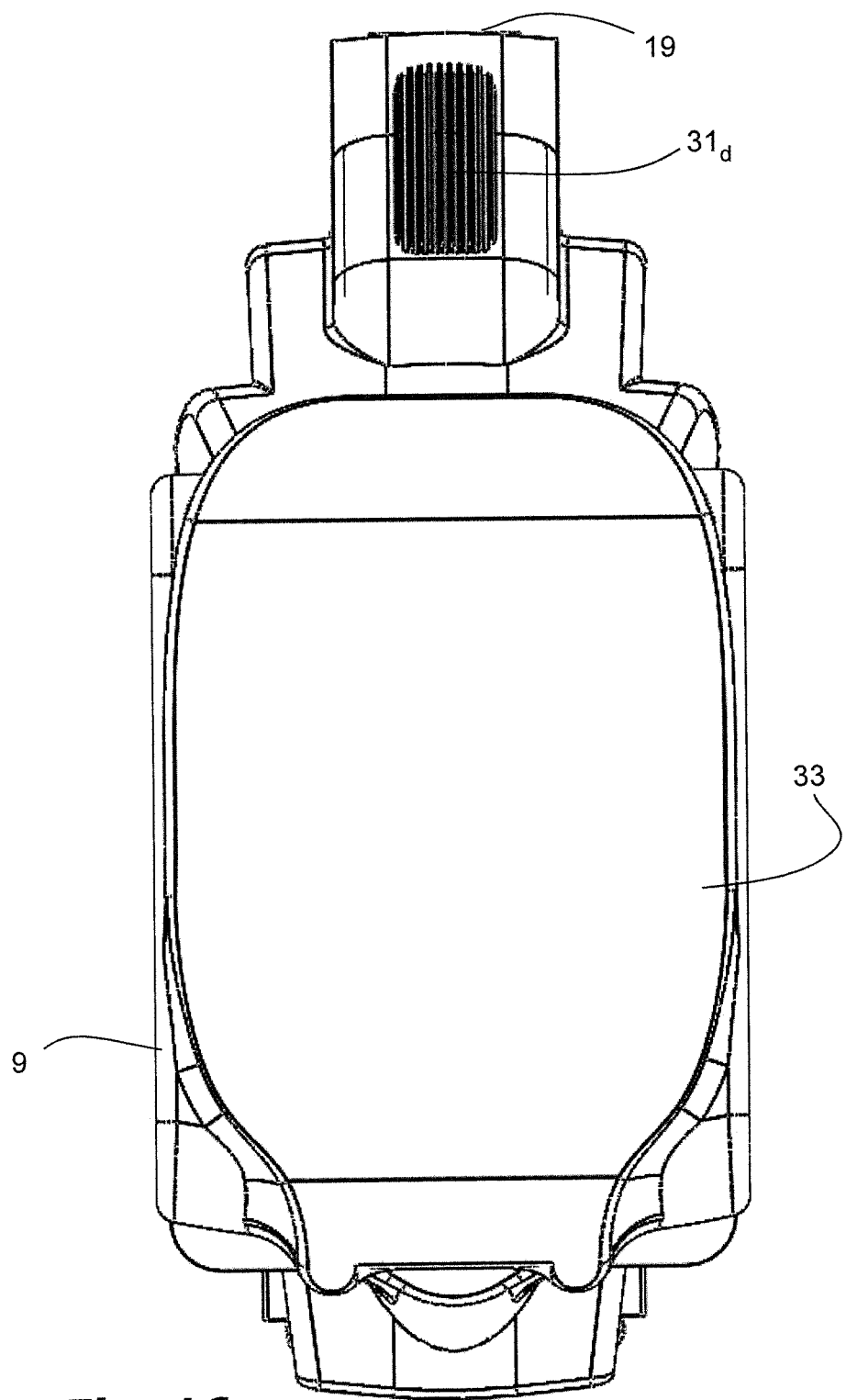
FIG. 16 is a schematic bottom view of an XRF analyzer with an attached battery, in accordance with an embodiment of the present invention.
Figure 17:
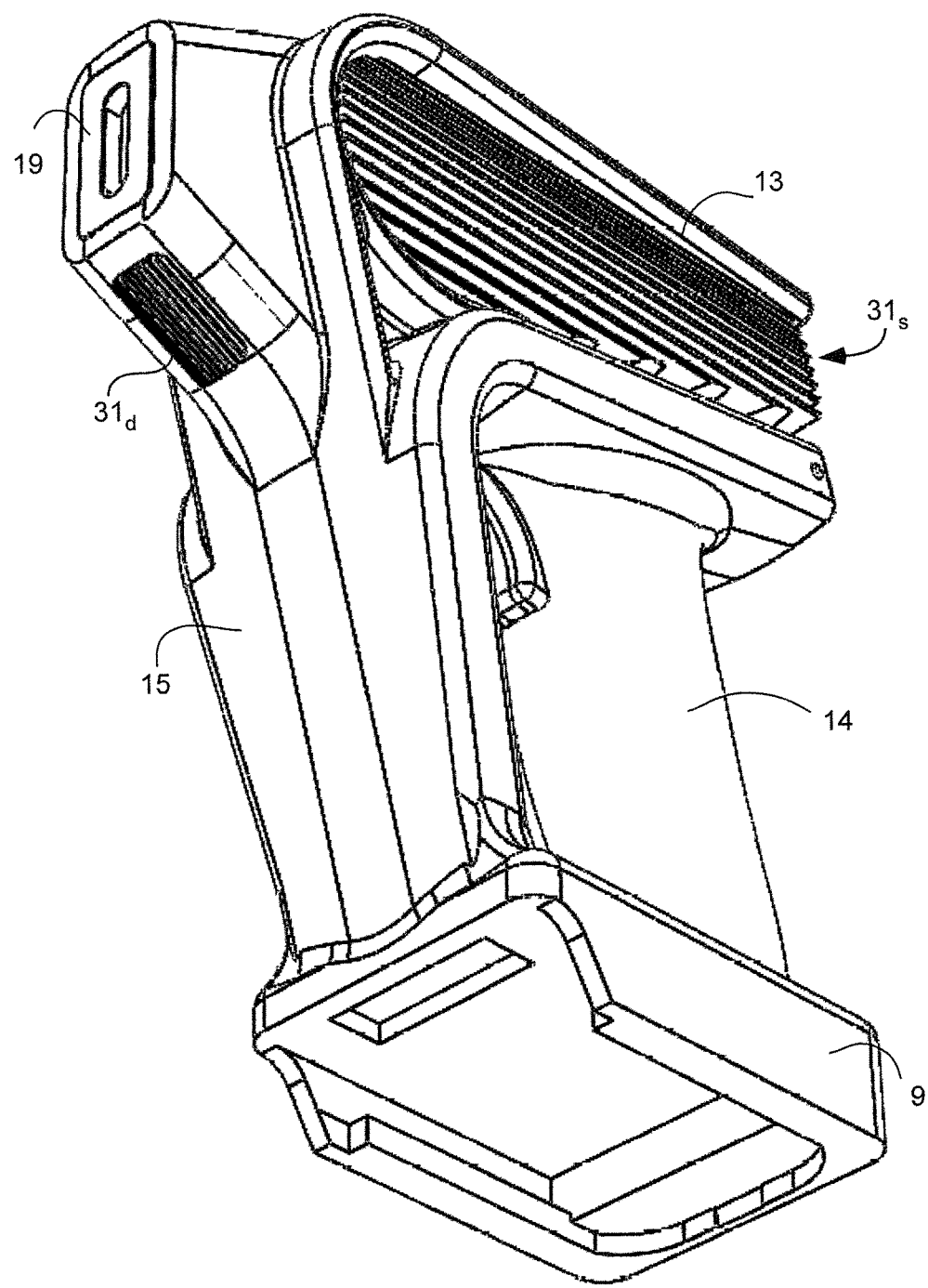
FIG. 17 is a schematic perspective view of an XRF analyzer without an attached battery, in accordance with an embodiment of the present invention.
Figure 18:
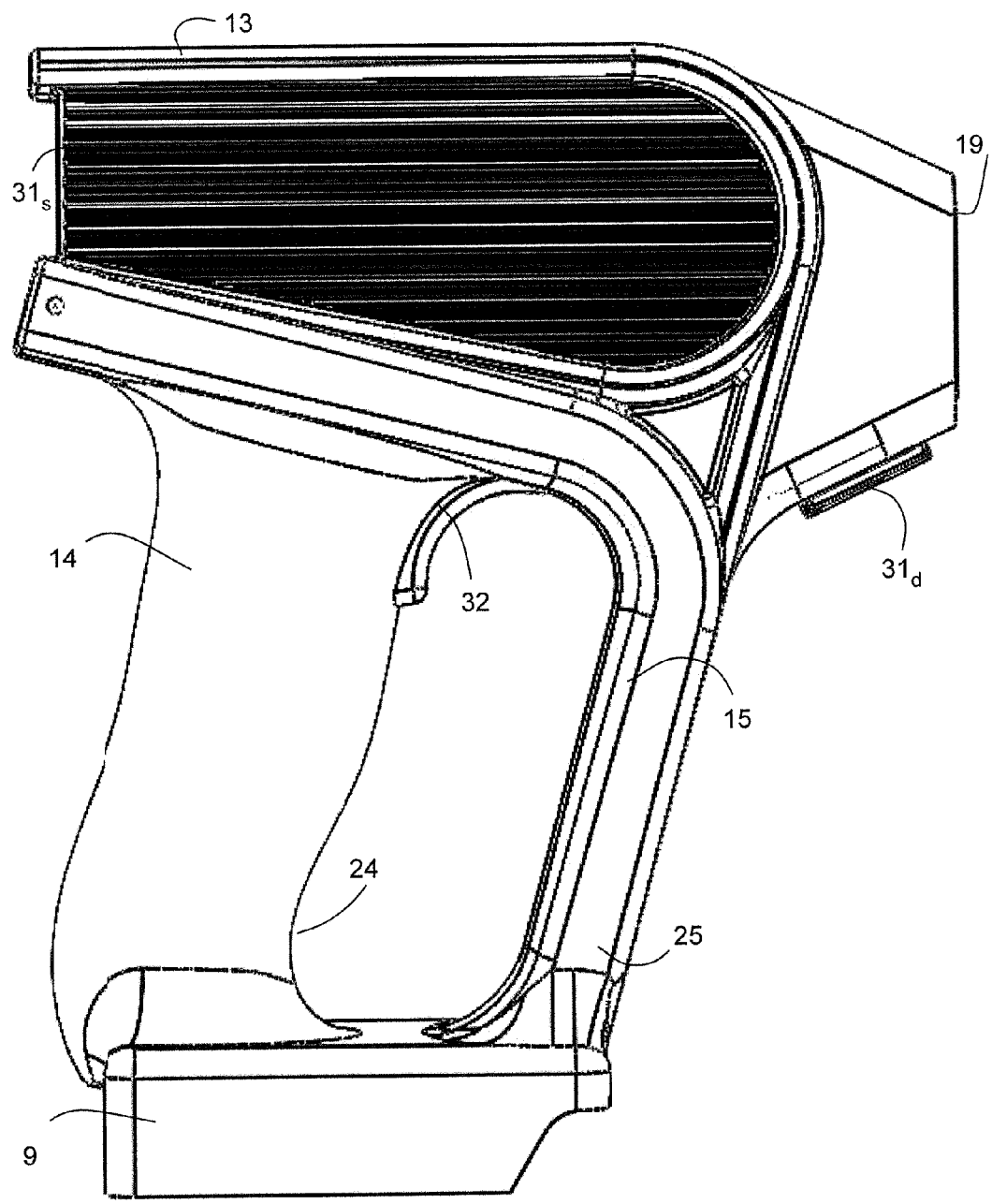
FIG. 18 is a schematic first side view of an XRF analyzer without an attached battery, in accordance with an embodiment of the present invention.
Figure 19:
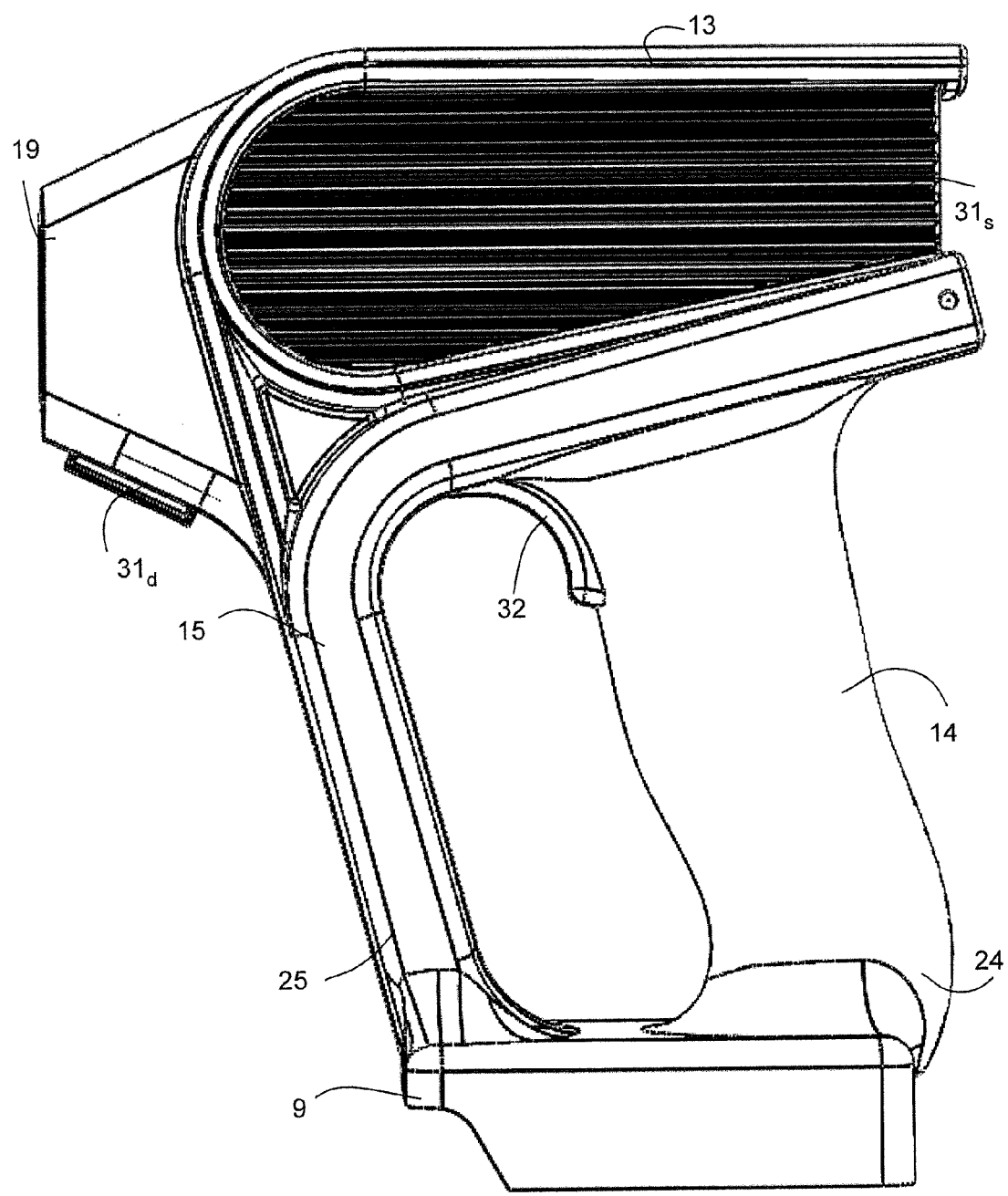
FIG. 19 is a schematic second side view of an XRF analyzer without an attached battery, in accordance with an embodiment of the present invention.
Figure 20:
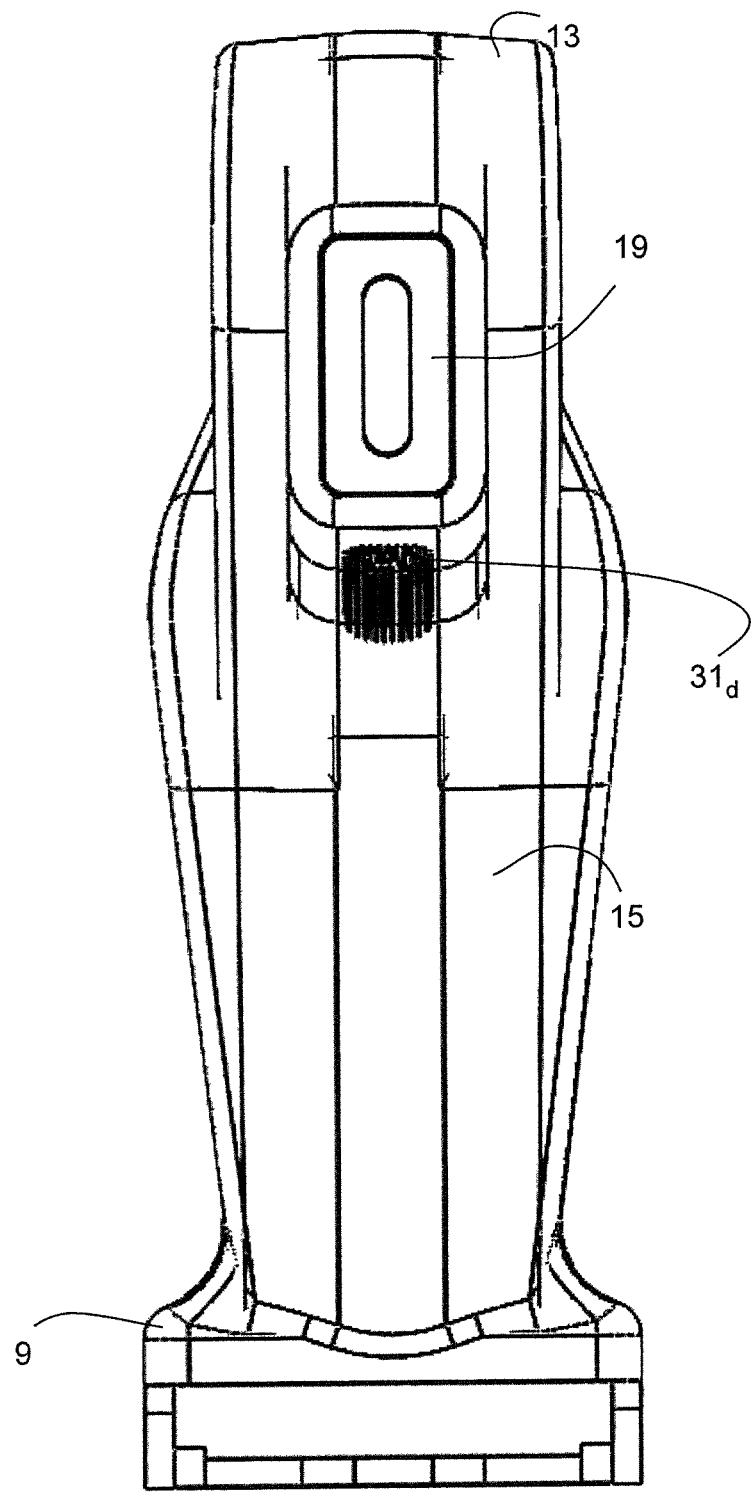
FIG. 20 is a schematic front view of an XRF analyzer without an attached battery, in accordance with an embodiment of the present invention.
Figure 21:
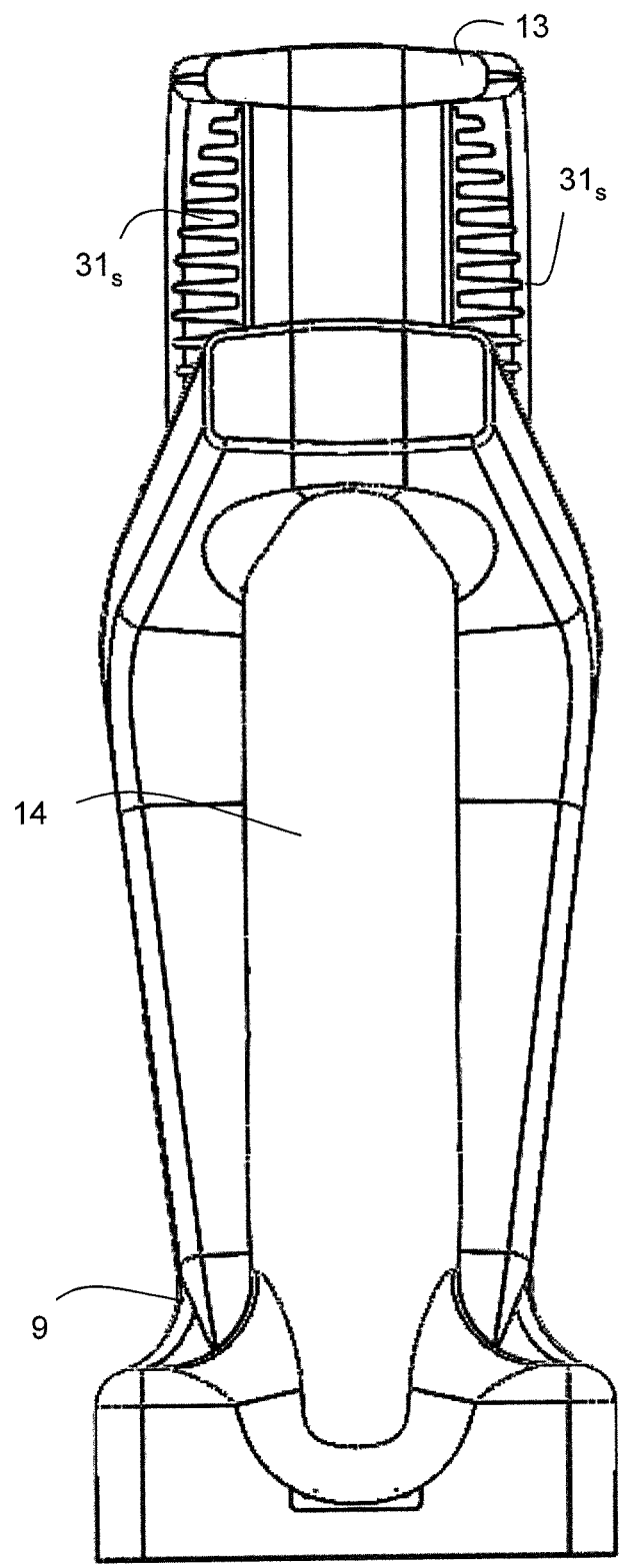
FIG. 21 is a schematic back view of an XRF analyzer without an attached battery, in accordance with an embodiment of the present invention.
Figure 22:
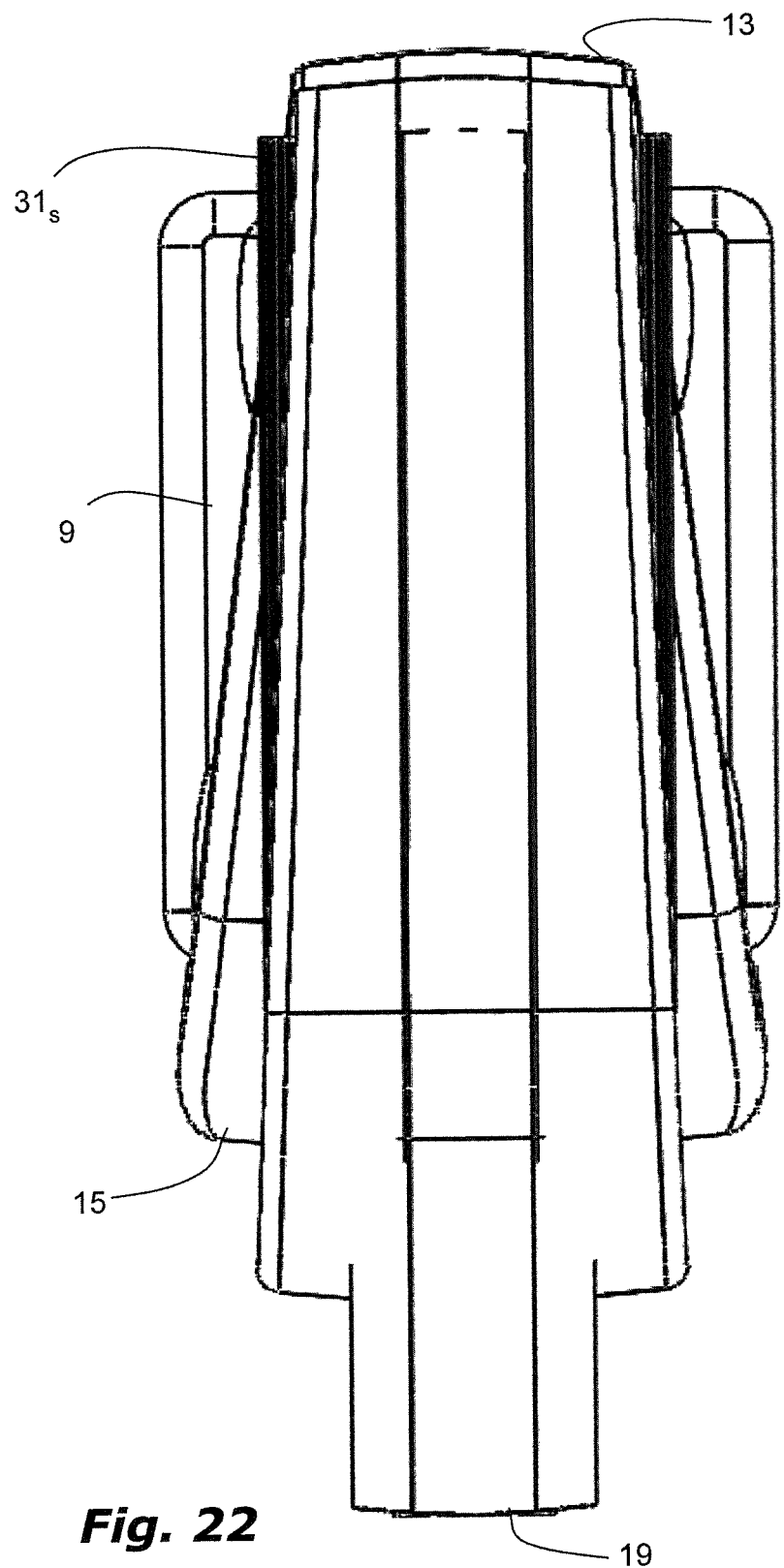
FIG. 22 is a schematic top view of an XRF analyzer without an attached battery, in accordance with an embodiment of the present invention.
Figure 23:
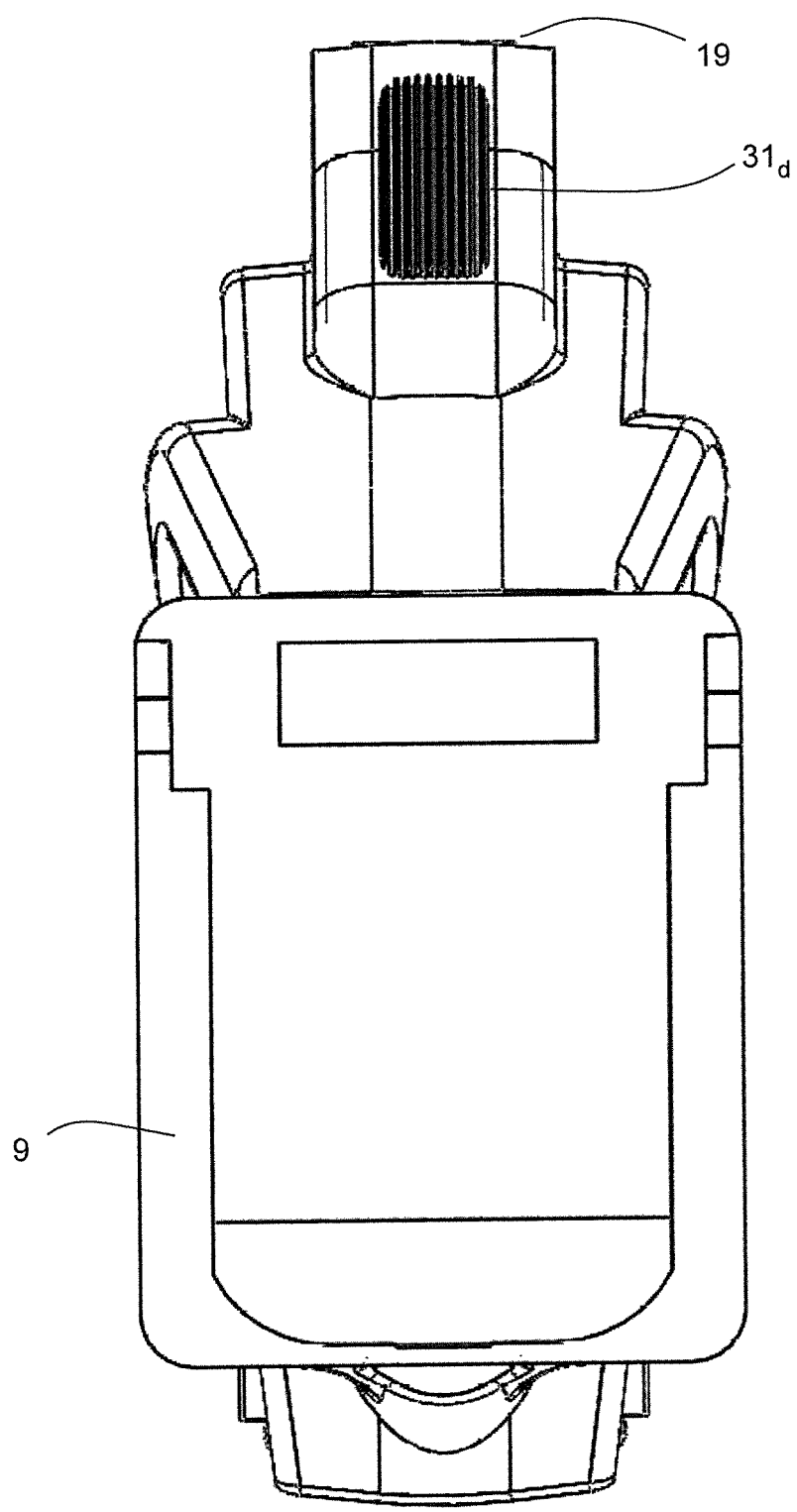
FIG. 23 is a schematic bottom view of an XRF analyzer without an attached battery, in accordance with an embodiment of the present invention.

As illustrated in FIGS. 1-3 and 5-9, portable x-ray fluorescence (XRF) analyzers 10, 20, 30, 50, 60, 70, 80, and 90 are shown comprising an engine component 13 having an x-ray emission end 19. The front view of an XRF analyzer in FIGS. 6, 13, and 20 shows the face of the x-ray emission end 19 (i.e. x-rays can emit from this front face). A handle 14 can extend from the engine component 13 to allow a user to hold and carry the XRF analyzer.

As shown in FIGS. 1-3, 5-7, and 9, a hand shield 15 can extend from the engine component 13 parallel to the handle 14. Thus, the handle 14 and the hand shield 15 can extend in two separate, parallel columns from the engine component 13 to a distal end (24 and 25 respectively—see FIGS. 2 and 7). The hand shield 15 can be located forward of the handle 14. The hand shield 15 can be disposed closer to the x-ray emission end 19 than the handle 14.

Figure 7:
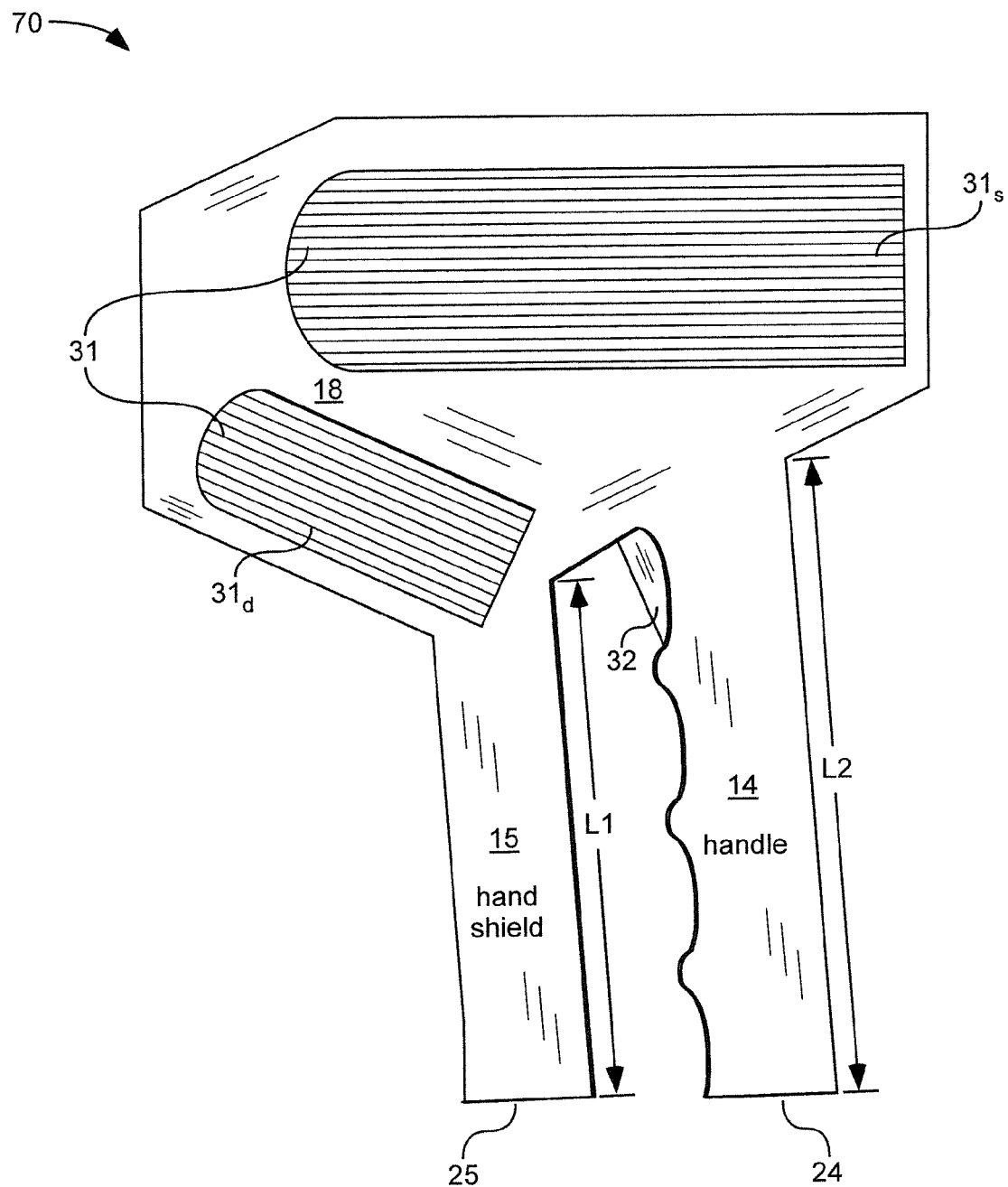
FIG. 7 is a schematic side view of an XRF analyzer, illustrating a hand shield and a handle extending from an engine component, in accordance with an embodiment of the present invention.

As shown in FIGS. 1-3, 5-6, and 9, the portable XRF analyzers 10, 20, 30, 50, 60, and 90 can further include a power component 9 spaced apart from engine component 13. The handle 14 and the hand shield 15 can attach the engine component 13 to the power component 9. Alternatively, as shown in FIG. 7, the handle 14 and the hand shield 15 need not be joined by a power component 9 at a distal end (24 and 25 respectively) from the engine component 13. Various factors such as aesthetics, ease of use, manufacturing considerations, durability, and cost may be considered in whether or not to include a power component joining the handle 14 and the hand shield 15 at a distal end (24 and 25 respectively) from the engine component 13.

The power component 9 can include electrical connections 17 configured for electrical connection to a portable, electric power-source 33. A portable, electric power-source 33 is shown in FIGS. 3 and 9-16. The portable, electric power-source 33 can be readily removable by the user. The portable, electric power-source 33 can be a battery.

Figure 3:
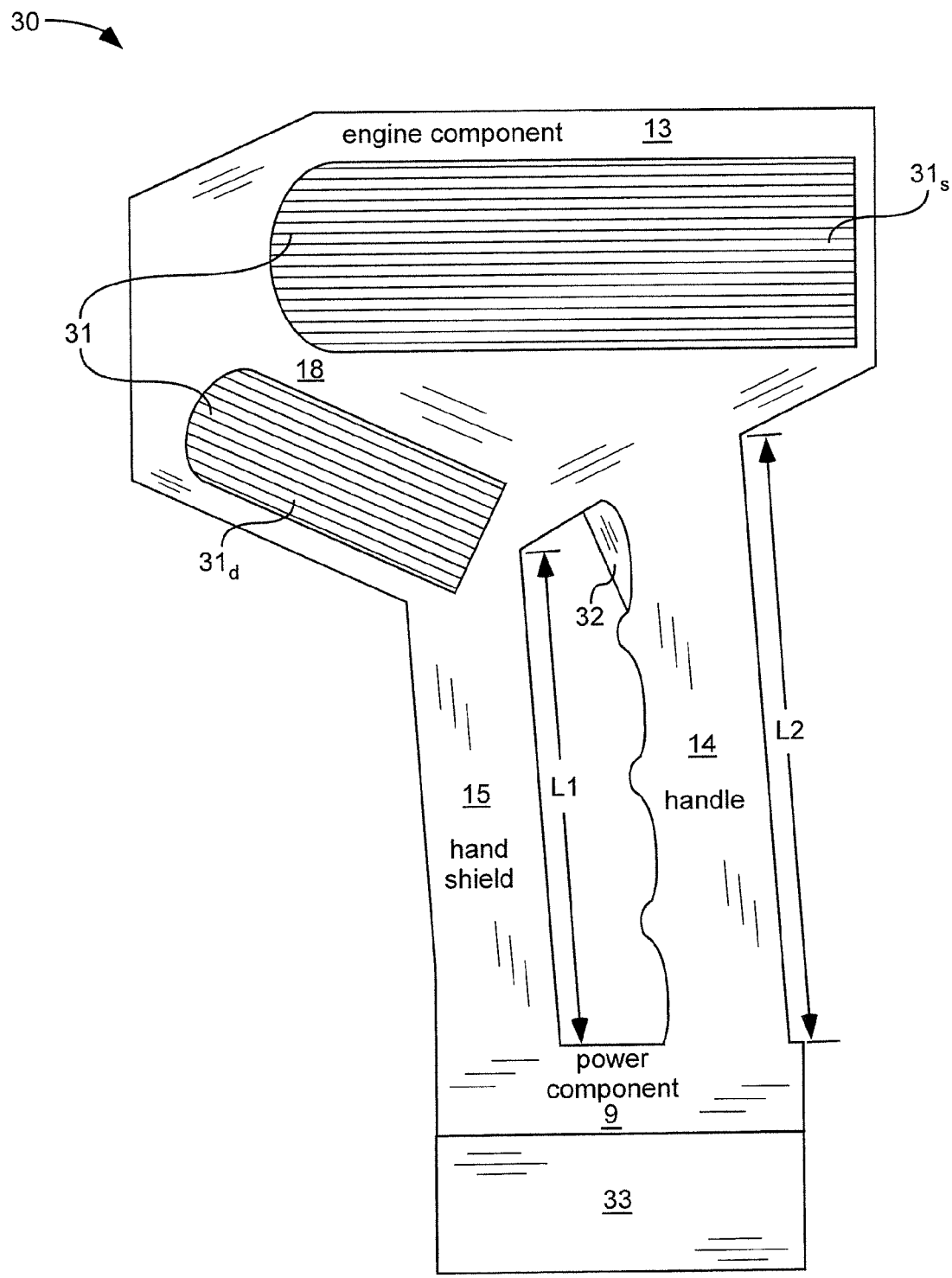
FIG. 3 is a schematic side view of an XRF analyzer, illustrating a heat sink disposed adjacent an x-ray source and a heat sink disposed adjacent an x-ray detector, in accordance with an embodiment of the present invention.

It can be ergonomically beneficial for the handle 14 and hand shield 15 to have a forward-leaning angle. As shown in FIGS. 3 and 7, the hand shield 15 can have a length L1 that is shorter than a length L2 of the handle 14 because of (a) the forward-leaning angle; (b) a shape of the engine component 13; and/or (c) a junction of the handle 14 and the hand shield 15 at the power component 9. For example, the hand shield 15 can have a length L1 that is between 60% and 90% of a length L2 of the handle 14 in one embodiment.

As shown in FIGS. 1, 4-6, & 9, an x-ray source 11 and an x-ray detector 12 can be disposed in and can be substantially enclosed by an engine component casing 13a and 13b. The x-ray source 11 can include an x-ray tube $11_t$ and an associated power supply $11_p$. The x-ray source 11 and the x-ray detector 12 can be oriented at an acute angle with respect to one another. The x-ray source 11 can be disposed in a location and oriented to emit x-rays 92 (FIG. 9) outward from an x-ray window $11_w$ (FIG. 6) portion of the x-ray tube $11_t$ disposed at the x-ray emission end 19 of the XRF analyzer towards a focal point 94 (FIG. 9) on a sample 91. The x-ray detector 12 can be disposed in a location and oriented to receive fluoresced x-rays 93 (FIG. 9) emitted from the focal point 94 on the sample 91. An amplifier, a digital pulse processor, and additional electronic components can analyze information from the x-ray detector for determination of material composition of the sample 91.

Figure 1:
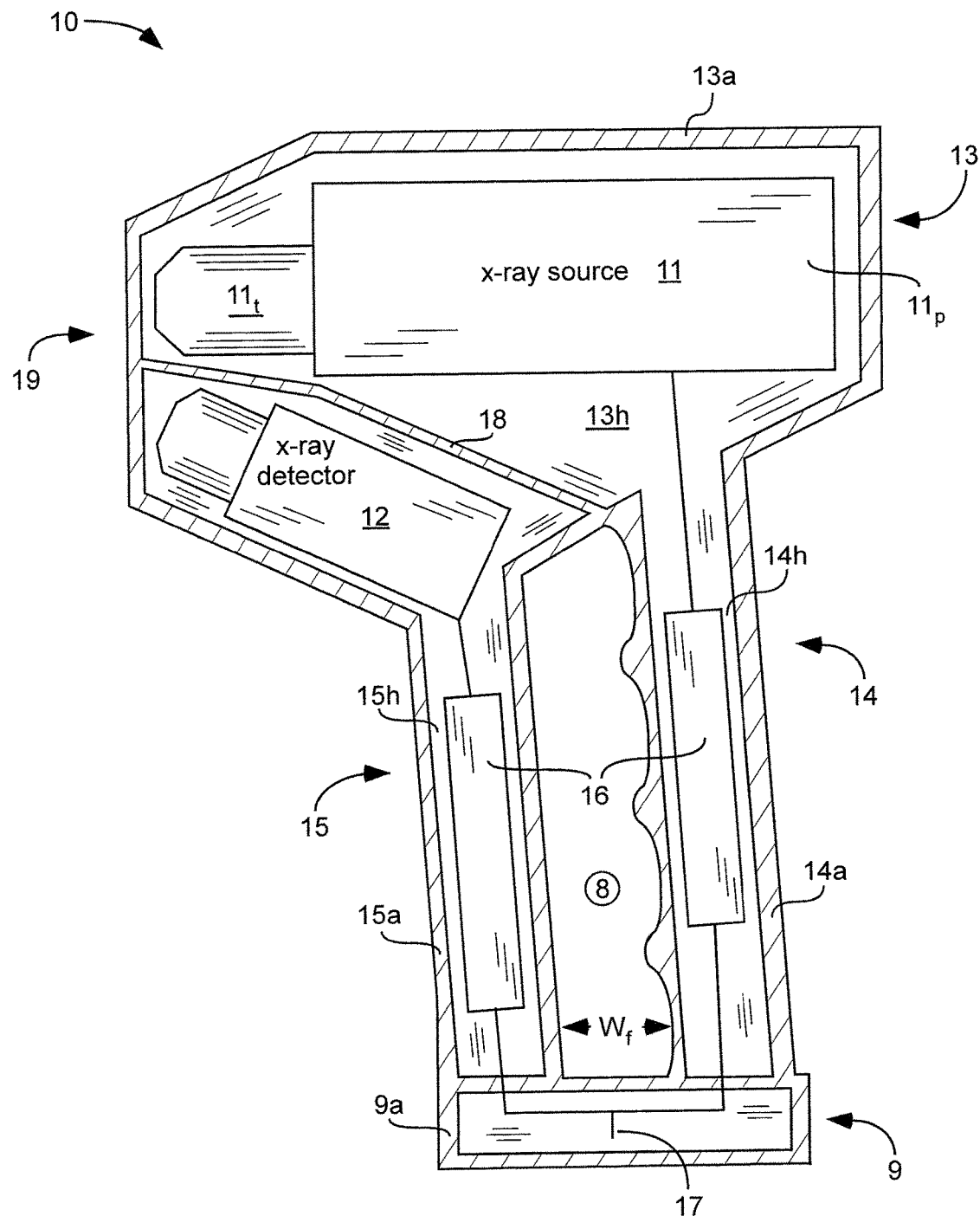
FIG. 1 is a schematic cross-sectional side view of an XRF analyzer, in accordance with an embodiment of the present invention.
Figure 2:
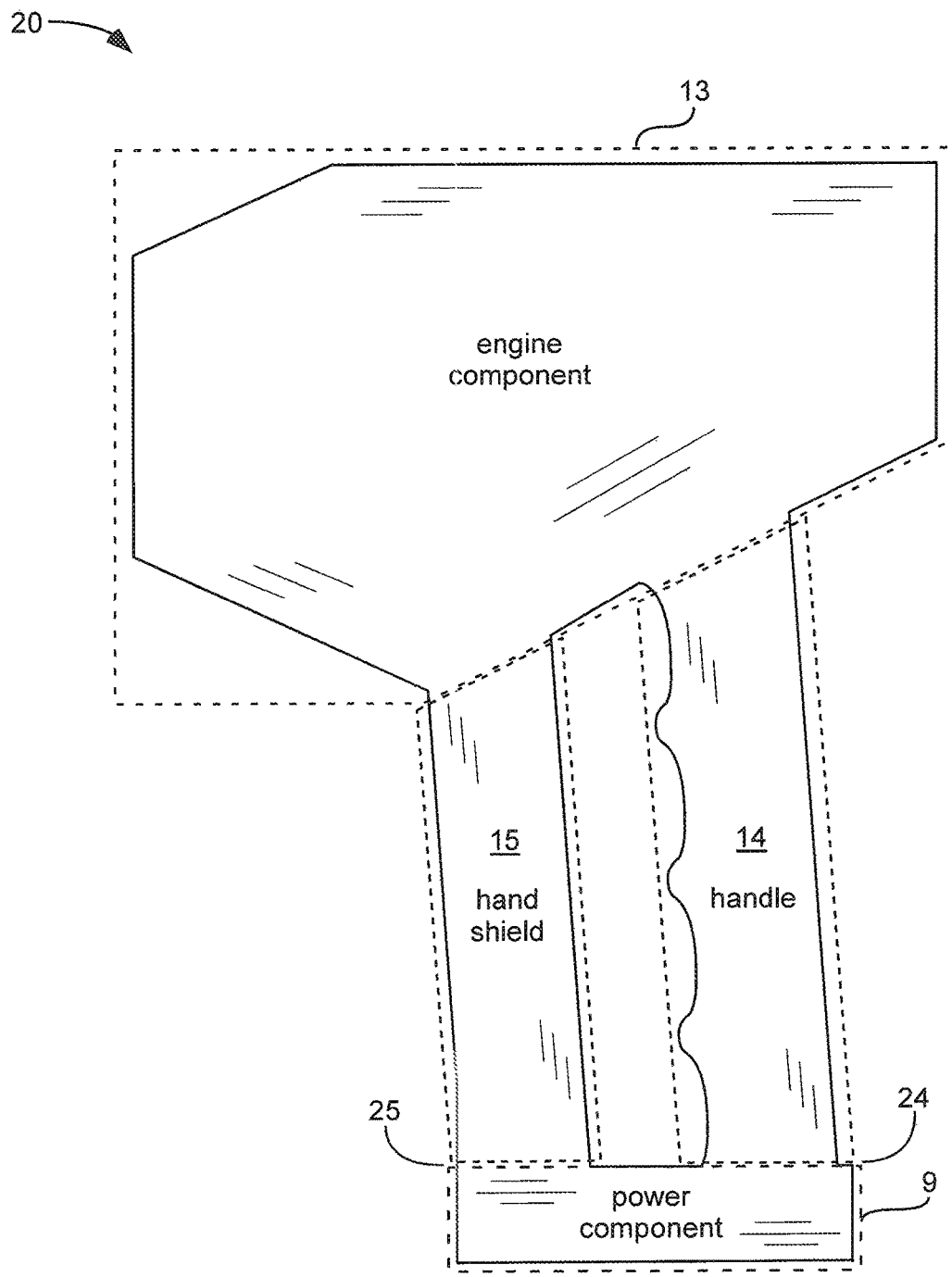
FIG. 2 is a schematic side view of an XRF analyzer, illustrating a hand shield and a handle extending between and attaching an engine component to a power component, in accordance with an embodiment of the present invention.

As shown in FIG. 1, there can be a finger gap 8 between the handle 14 and the hand shield 15. As used herein, "finger gap" means a gap that is large enough to allow a user's fingers to be inserted into the gap to grasp the handle 14. In one embodiment, the finger gap 8 can have a width $W_f$ that is between 25 mm and 80 mm.

The hand shield 15 can be disposed closer to the x-ray emission end 19 than the handle 14. The hand shield 15 can be disposed in a location to substantially block (a) x-rays 93 emitted from the sample 91 to be analyzed, or (b) x-rays 92 emitted from the x-ray tube $11_t$ (including x-rays emitted from sides of the x-ray tube $11_t$) from impinging on a hand 95 of a user while grasping the handle 14 (see FIG. 9). A casing 15a and 15b of the hand shield 15 ("hand shield casing" means 15a and 15b combined) and a casing 13a and 13b of the engine component 13 ("engine component casing" means 13a and 13b combined) can comprise a material for blocking x-rays (see casing in FIGS. 1 & 4). For example, the material for blocking x-rays can comprise plastic impregnated with tungsten, tantalum, molybdenum, or combinations thereof. As another example, the material for blocking x-rays can comprise a plastic impregnated with an element having an atomic number of at least 42. The XRF analyzer can be designed, based on x-ray source 11 voltage and hand shield 15 thickness and material, to block (i.e. prevent from passing through the hand shield 15) at least 99% of incoming x-rays in one aspect, or at least 99.8% of incoming x-rays in another aspect, or at least 99.98% of incoming x-rays in another aspect.

As shown on XRF analyzer 50 in FIG. 5, the hand shield 15 can have a width $W_s$ that is at least as large as a width $W_h$ of the handle 14 in order to block x-rays from hitting a hand of the user. In one embodiment, the hand shield 15 can have a width that is at least 50% wider than a width $W_h$ of the handle 14. In another embodiment, the hand shield 15 can have a width $W_s$ that is at least as large as a width $W_h$ of the handle 14 along at least 50% of a length L1 of the hand shield 15 from the engine component. In another embodiment, the hand shield 15 can have a width $W_h$ that is at least 50% wider than a width $W_h$ of the handle 14 along at least 50% of a length L1 of the hand shield 15. Hand shield length L1 and handle length L2 are shown in FIGS. 3 and 7.

The hand shield can be useful not only for blocking x-rays from impinging on a hand of the user, but also for storage of electronic components. As shown in FIG. 1, there can be a hollow 15h in the hand shield 15 and/or a hollow 14h in the handle 14. The hollow 15h in the hand shield 15 and/or the hollow 14h in the handle 14 can be sized and shaped to receive electronic component(s) 16. Electronic component(s) 16 can be disposed in the hand shield 15 and/or the handle 14. The electronic component(s) 16 can be configured for operation of the x-ray source 11, the x-ray detector 12, or both. A hollow 13h in the engine component 13 can be interconnected with a hollow 15h in the hand shield 15 and/or a hollow 14h in the handle 14.

The electronic component(s) 16 can include a digital pulse processor electrically connected to the x-ray detector 12. The x-ray detector 12 can include a semiconductor chip (e.g. PIN diode or SDD) for receiving x-rays 93 and a signal amplifier for amplifying incoming x-ray signals. A digital pulse processor can be electrically connected to the signal amplifier. The digital pulse processor can convert the amplified signal into meaningful data to indicate the energy of incoming x-rays. For improved signal quality by avoiding noise interference, it can be beneficial to dispose the digital pulse processor near the signal amplifier. Disposing the digital pulse processor in the hand shield 15 can allow the digital pulse processor to be disposed near the signal amplifier, thus improving signal quality.

Figure 8:
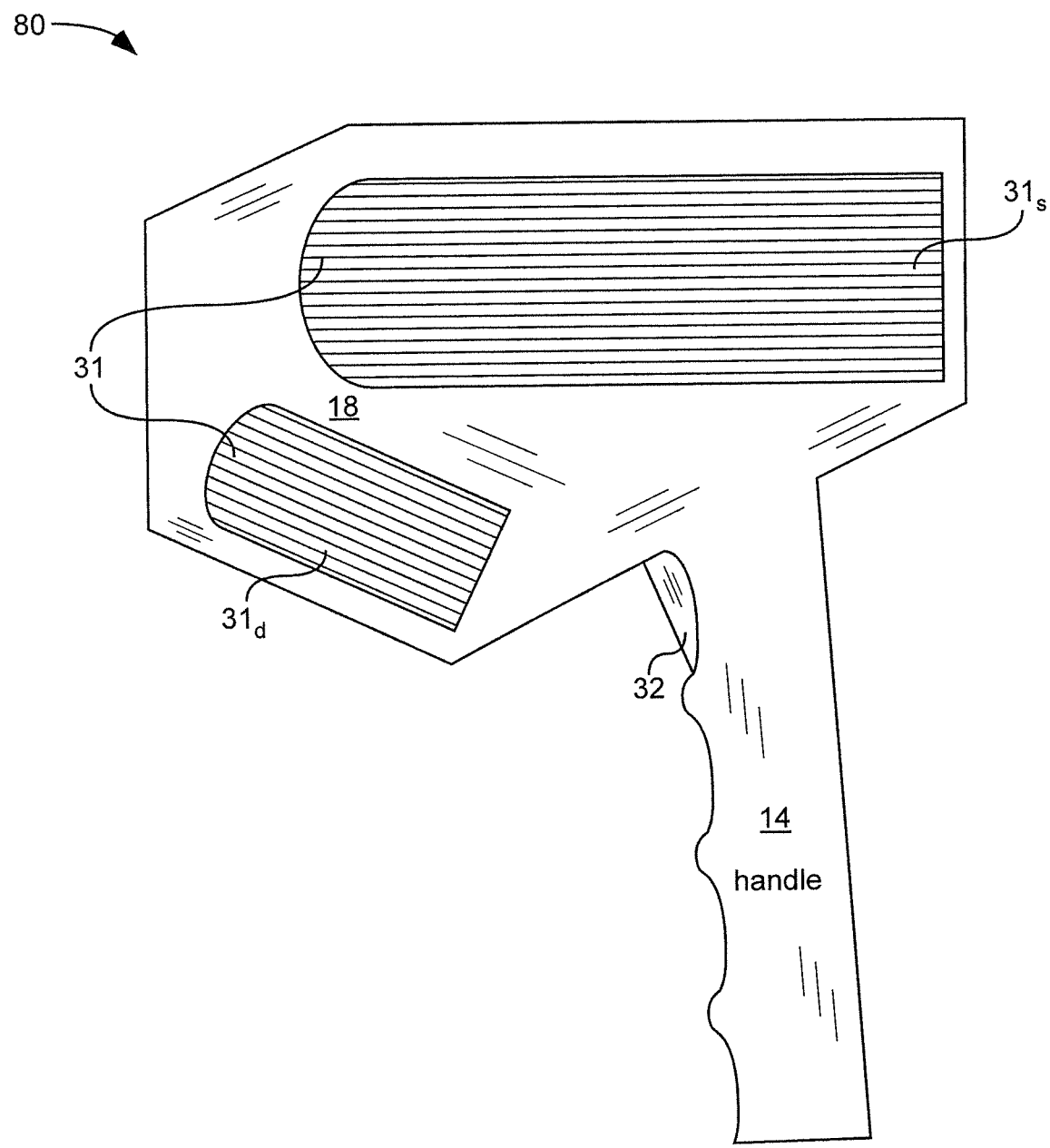
FIG. 8 is a schematic side view of an XRF analyzer with two heat sinks and a handle extending from an engine component, in accordance with an embodiment of the present invention.
Figure 9:
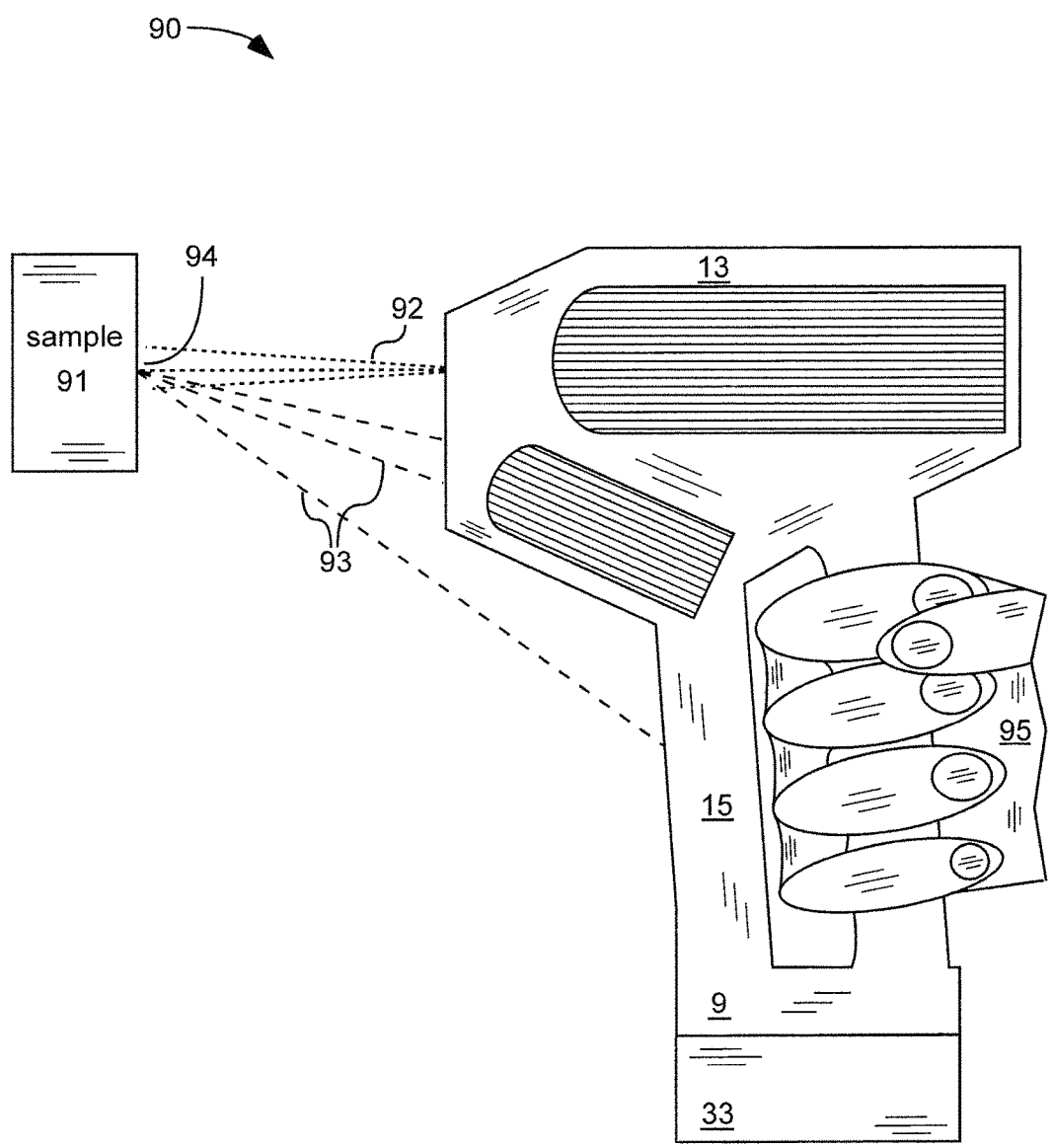
FIG. 9 is a schematic side view of an XRF analyzer, illustrating emission of x-rays towards a sample and x-rays fluorescing back to the XRF analyzer, in accordance with an embodiment of the present invention.
Figure 10:
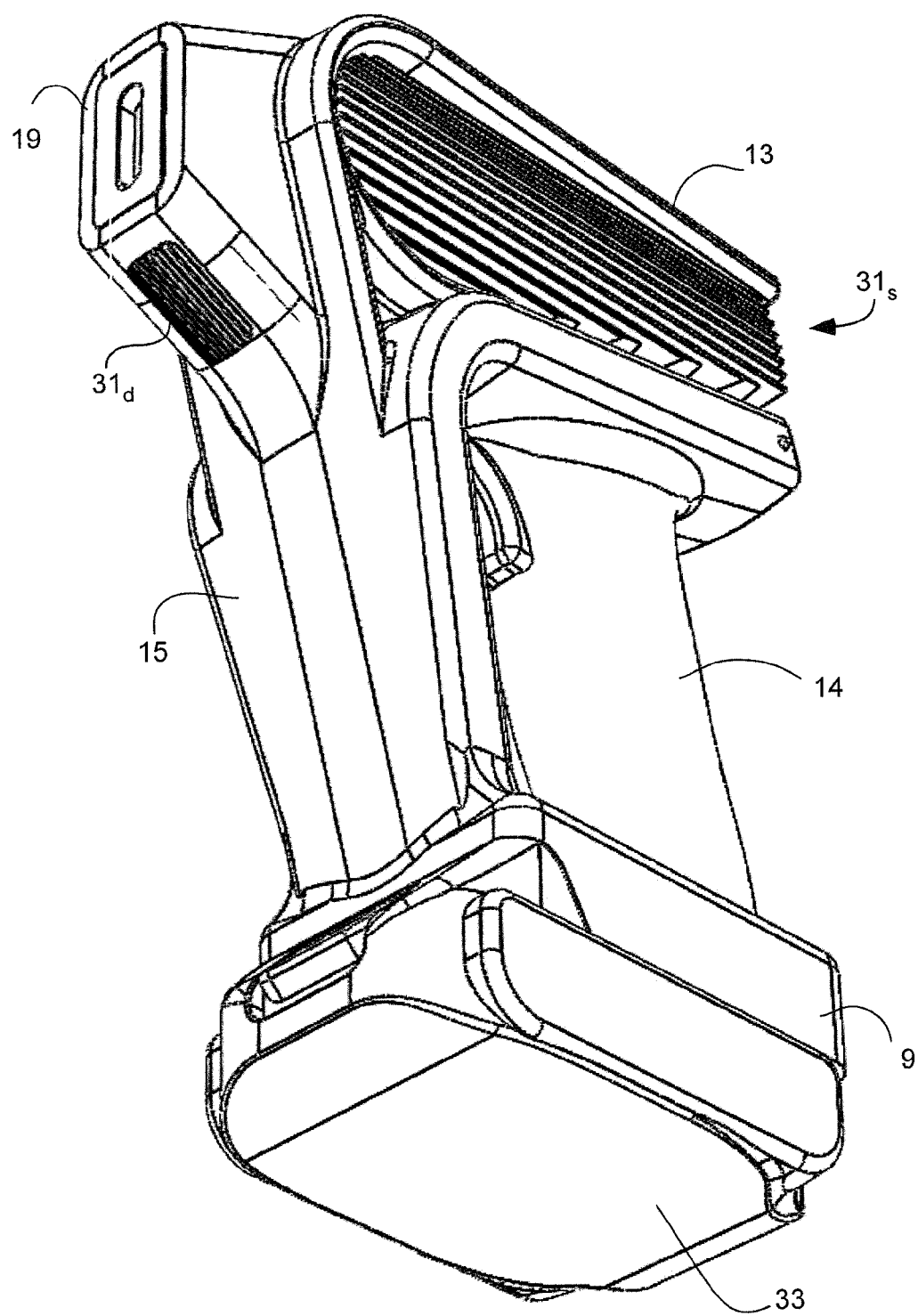
FIG. 10 is a schematic perspective view of an XRF analyzer with an attached battery, in accordance with an embodiment of the present invention.
Figure 11:
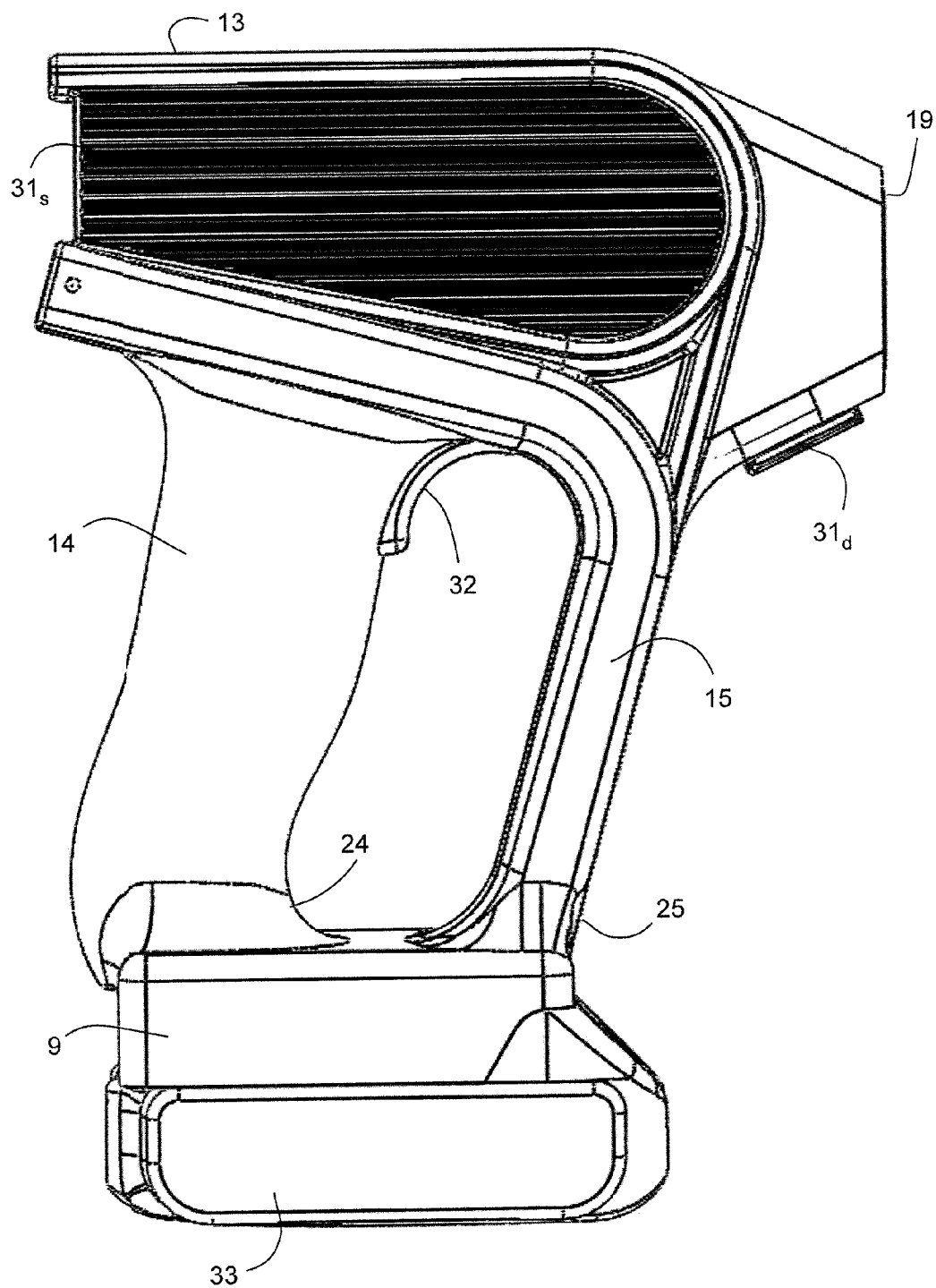
FIG. 11 is a schematic first side view of an XRF analyzer with an attached battery, in accordance with an embodiment of the present invention.
Figure 12:
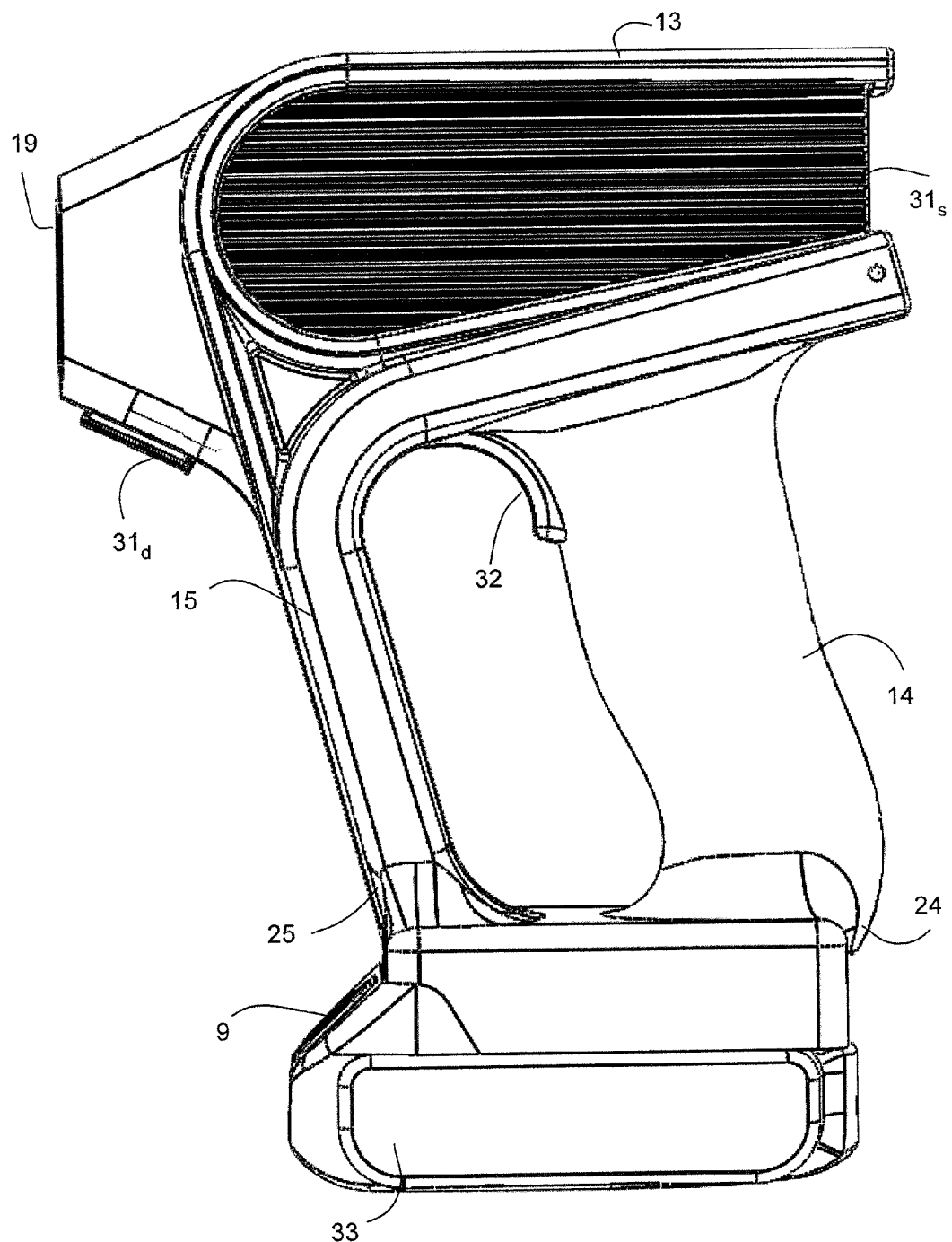
FIG. 12 is a schematic second side view of an XRF analyzer with an attached battery, in accordance with an embodiment of the present invention.

As shown on XRF analyzers 30, 70, and 80 in FIGS. 3, 7, and 8, the handle 14 can include a switch 32, such as a trigger for example, to cause the XRF analyzer to emit x-rays 92 from the x-ray source 11.

Figure 4:
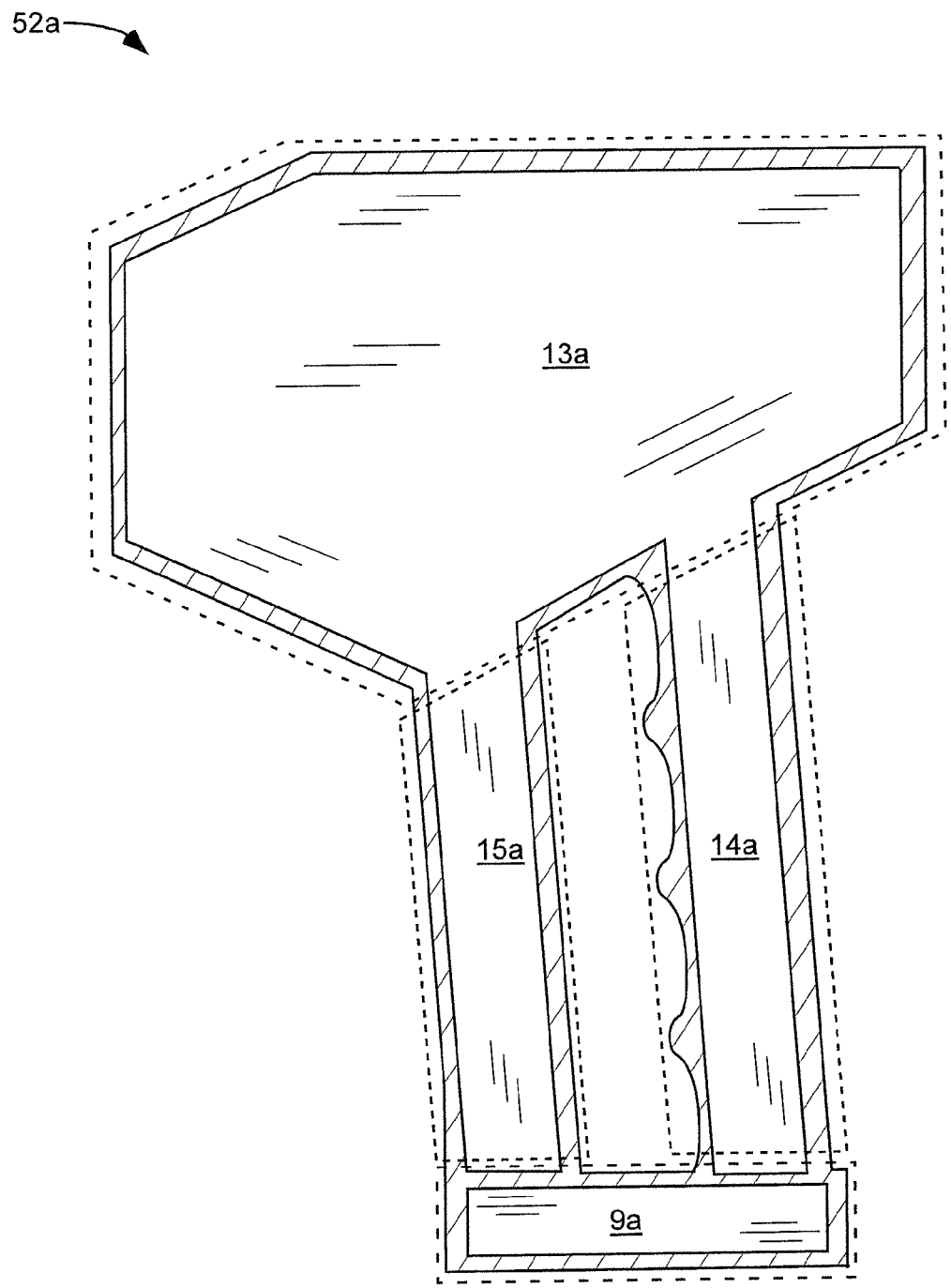
FIG. 4 is a schematic cross-sectional side view of half of a housing of an XRF analyzer, showing an inside of the housing, in accordance with an embodiment of the present invention.

As shown in FIGS. 4-6, an XRF analyzer housing can be formed in two halves, or two separate portions 52a and 52b. The portions need not necessarily divide equally into halves—one portion can be more than half and the other portion can be less than half, which joined together make a whole. Each portion 52a or 52b can include:
1. a section of the engine component casing 13a or 13b ("engine component casing section" means either 13a or 13b);
2. if a power component is used—a section of a casing 9a or 9b of the power component 9 ("power component casing section" means 9a or 9b);
3. a section of the hand shield casing 15a or 15b ("hand shield casing section" means 15a or 15b); and
4. a section of a casing 14a or 14b of the handle 14 ("handle casing section" means 14a or 14b).

Each portion 52a and 52b can be integrally formed in a single, monolithic body that was formed together at the same time. For example, one portion 52a can be formed at one time, such as by injection molding, as one single, monolithic body. The other portion 52b can also be formed at one time, such as by injection molding, as a separate single, monolithic body. After insertion of components (e.g. x-ray source 11 and x-ray detector 12), the portions 52a and 52b can be joined by a fastener or adhesive.

By forming the hand shield casing section 15a (or 15b) and the engine component casing section 13a (or 13b) together, both sections can include a material for blocking x-rays. Manufacturing by this method (e.g. forming each portion as a single, monolithic body then joining the two portions 52a and 52b) can be simple and cost-effective and can result in sturdy housing.

As shown on XRF analyzers 30, 50, 60, 70, 80, and 90 in FIGS. 3 and 5-9, at least one heat sink 31 can be used to draw heat away from the x-ray source 11 and/or the x-ray detector 12. Heat sinks 31 are also shown in FIGS. 10-23.

In one embodiment, the heat-sink(s) can be finned. The heat sinks can be made of any material with sufficiently high thermal conductivity. For example, the heat sinks can be made of or can comprise aluminum due to its high thermal conductivity and low cost.

An x-ray source heat-sink $31_s$ can be disposed in an opening in the engine component casing 13a or 13b and over a side of the x-ray source 11. One x-ray source heat-sink $31_{sa}$ can be disposed on one side of the x-ray source 11 and another x-ray source heat-sink $31_{sb}$ can be disposed on an opposite side of the x-ray source 11, as shown in FIGS. 5-6.

An x-ray detector heat-sink $31_d$ can be disposed in an opening in the engine component casing 13a or 13b and adjacent or over a side of the x-ray detector 12. One x-ray detector heat-sink $31_d$ can be disposed on one side of the x-ray source 11 and another x-ray source heat-sink $31_s$ can be disposed on an opposite side of the x-ray source 11. An x-ray detector heat-sink $31_d$ can be disposed at a front-face (x-ray emission end 19) of the XRF analyzer as shown in FIGS. 10-13, 16-20, and 23.

Heat transferred between the x-ray detector 12 and the x-ray source 11 can adversely affect x-ray detector 12 resolution. In order to minimize such heat transfer, the x-ray source 11 and the x-ray source heat sink $31_s$ can be separated from the x-ray detector 12 and the x-ray detector heat sink $31_d$ by thermally insulating material. This thermally insulating material can be a segment 18 of the engine component casing 13a or 13b (see FIGS. 1 and 3). This segment 18, all of the engine component casing 13a and 13b, or all of the housing 52a and 52b can have a relatively low thermal conductivity, such as for example a thermal conductivity of less than 5 W/(m*K) in one aspect, less than 10 W/(m*K) in another aspect, or less than 20 W/(m*K) in another aspect. Nylon is one possible material that may be suitable for the engine component casing 13a and 13b or all of the housing 52a and 52b. Distance between the x-ray detector 12 and the x-ray source 11 and thickness of the thermally insulating material can also minimize such heat transfer. For example, the x-ray source heat-sink $31_s$ can be separated from the x-ray detector heat sink $31_d$ by at least 3 millimeters of the thermally insulating material.

Although the hand shield 15 can be beneficial for reducing the user's exposure to x-rays, the hand shield 15 can be omitted, especially if low-energy x-rays will be used, or the user's time of exposure is small. Shown in FIG. 8 is an XRF analyzer without a hand shield. This embodiment includes at least one heat sink 31. There can be two or more heat sinks 31. An x-ray detector heat sink $31_d$ and an x-ray source $31_s$ heat sink can be separated from each other by thermally insulative material as was discussed above.

Figure 24:
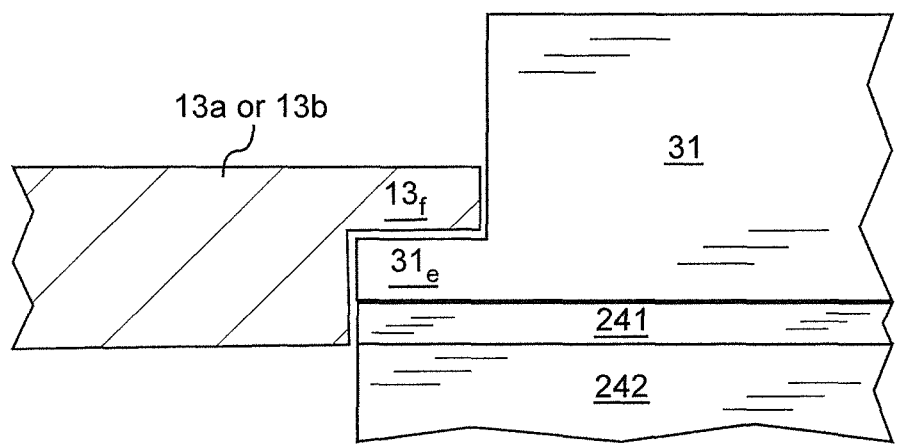
FIG. 24 is a schematic cross-sectional side view of an engine component casing flange holding a heat sink in place, in accordance with an embodiment of the present invention.

As shown in FIG. 24, the heat sink(s) 31 can be secured in place by a flange-portion $13_f$ of the engine component casing 13a or 13b. An edge $31_e$ of the heat sink 31 can be disposed under the flange-portion $13_f$, thus holding the heat sink 31 in place.

Air between a heat source 242 (the x-ray source 11 or the x-ray detector 12) and the heat sink 31 can reduce heat transfer. As shown in FIG. 24, a compressible gap pad 241 can be disposed between and can adjoin or touch both the heat source 242 and the heat sink 31. The compressible gap pad 241 can substantially fill the air gap. The compressible gap pad 241 can provide a path of relatively high thermal conductivity between the heat source 242 and the heat sink 31. The gap pad 241 can have a relatively high thermal conductivity (substantially higher than air). For example, thermal conductivity of the gap pad can be between 0.8 W/(m*K) and 5 W/(m*K) in one aspect, or at least 0.75 W/(m*K) in another aspect.

Method

A method, of assembling a portable x-ray fluorescence (XRF) analyzer, can comprise some or all of the following steps (see FIGS. 1, 4-6, and 9):

1. injection molding, with a plastic impregnated with an element having an atomic number of at least 42, an XRF analyzer housing in two separate portions 52a and 52b:
    a. each portion 52a and 52b including an engine component casing section (13a or 13b) attached to a power component casing section (9a or 9b) by a handle casing section (14a or 14b) and a hand shield casing section (15a or 15b); and
    b. wherein the handle casing section (14a or 14b) and the hand shield casing section (15a or 15b) extend in two separate, parallel columns between the engine component casing section (13a or 13b) and the power component casing section (9a or 9b);
2. attaching the two XRF analyzer portions 52a and 52b to each other (see seam or junction 51) and sandwiching between the two engine component casing sections (13a and 13b) an x-ray source 11 and an x-ray detector 12 such that:
    a. the x-ray source 11 is disposed in a location to emit x-rays 92 outward from the XRF analyzer towards a sample 91;
    b. the x-ray detector 12 is disposed in a location to receive fluoresced x-rays 93 emitted from the sample 91;
    c. the two hand shield casing sections (15a and 15b) form a hand shield 15;
    d. the two handle casing sections (14a and 14b) form a handle 14; and
    e. the hand shield 15 is disposed closer to an x-ray emission end 19 of the x-ray source than the handle 14.
3. disposing an x-ray source heat sink $31_s$ over the x-ray source 11 in an opening in the housing;
4. disposing an x-ray detector heat sink $31_d$ over the x-ray detector 12 in an opening in the housing; and
5. disposing a segment 18 of the housing between the x-ray source heat sink $31_s$ and the x-ray detector heat sink $31_d$.

What is claimed is:

1. A portable X-ray fluorescence (XRF) analyzer comprising
    a. an engine component having an x-ray emission end and a power component spaced-apart from each other;
    b. a handle and a hand shield:
        i. extending in parallel between the engine component and the power component;
        ii. attaching the engine component to the power component; and
        iii. defining a finger gap therebetween;
    c. the hand shield disposed closer to the x-ray emission end than the handle;
    d. a hand shield casing and an engine component casing comprising a material for blocking x-rays;
    e. an x-ray source and an x-ray detector disposed in and substantially enclosed by the engine component casing;
    f. the x-ray source disposed in a location and oriented to emit x-rays outward from the x-ray emission end towards a sample;
    g. the x-ray detector disposed in a location and oriented to receive fluoresced x-rays emitted from the sample;
    h. the power component including electrical connections configured for electrical connection to a portable, electric power-source;
    i. hollow formed in the hand shield, the hand shield casing forming a perimeter around at least a majority of the hollow;
    j. an electronic component disposed the hollow of the hand shield; and
    k. the electronic component configured for operation of the x-ray source, the x-ray detector, or both.
2. The XRF analyzer of claim 1, further comprising:
    l. two housing portions, each housing portion comprising:
        i. an engine component casing section;
        ii. a power component casing section;
        iii. a hand shield casing section; and
        iv. a handle casing section;
    m. the engine component casing section, the power component casing section, the hand shield casing section, and the handle casing section of each housing portion being integrally formed in a single, monolithic body formed together at the same time with the hand shield casing section and the handle casing section of each housing portion extending in parallel between and attaching to the engine component casing section and the power component casing section of each housing portion; and
    n. the two housing portions joined together to form an XRF analyzer housing.
3. The XRF analyzer of claim 1, wherein the material for blocking x-rays comprises plastic impregnated with tungsten, tantalum, molybdenum, or combinations thereof.
4. The XRF analyzer of claim 1, wherein the hand shield has a width that is at least as large as a width of the handle along at least 50% of a length of the hand shield.
5. The XRF analyzer of claim 1, wherein the electronic component includes a digital pulse processor electrically connected to the x-ray detector.
6. The XRF analyzer of claim 1, further comprising:
    l. an x-ray source heat-sink disposed in an opening in the engine component casing and adjacent a side of the x-ray source;
    m. an x-ray detector heat-sink disposed in another opening in the engine component casing and adjacent a side of the x-ray detector;
    n. the x-ray source heat-sink separated from the x-ray detector heat sink by a segment of the engine component, casing having a thermal conductivity of less than 10 W/(m*K).
7. A portable x-ray fluorescence (XRF) analyzer comprising:
    a. an engine component having an x-ray emission end and an engine component casing;
    b. an x-ray source and an x-ray detector disposed in and substantially enclosed by the engine component casing;
    c. the x-ray source disposed in a location and oriented to emit x-rays outward from the x-ray emission end towards a sample;
    d. the x-ray detector disposed in a location and oriented to receive fluoresced x-rays emitted from the sample;
    e. a handle extending form the engine component to allow a user to hold and carry the XRF analyzer;
    f. a hand shield extending from the engine component, parallel to the handle, and disposed closer to the x-ray emission end than the handle;
    g. a finger-gap between the handle and the hand shield;

h. a hand shield casing and the engine component casing including a material for blocking x-rays;
i. an x-ray source heat-sink disposed in an opening in the engine component casing and adjacent a side of the x-ray source;
j. an x-ray detector heat-sink disposed in another opening in the engine component casing and adjacent a side of the x-ray detector; and
k. the x-ray source heat-sink separated from the x-ray detector heat sink by a segment of the engine component casing having a thermal conductivity of less than 10 W/(m*K).

8. The XRF analyzer of claim 7, further comprising:
l. two housing portions, each housing portion comprising:
   i. an engine component casing section;
   ii. a handle casing section extending from the engine component casing section; and
   iii. a hand shield casing section extending from the engine component casing section, parallel to the handle casing section;
m. the engine component casing section, the hand shield casing section, and the handle casing section of each housing portion being integrally formed in a single, monolithic body formed together at the same time;
n. the two housing portions joined together to form an XRF analyzer housing.

9. The XRF analyzer of claim 7, wherein an engine component casing section, a hand shield casing section, and a handle casing section are integrally formed in a single, monolithic body that was formed together at the same time.

10. The XRF analyzer of claim 7, wherein the material for blocking x-rays comprises plastic impregnated with tungsten, tantalum, molybdenum, or combinations thereof.

11. The XRF analyzer of claim 7, wherein the hand shield has a length that is between 60% and 90% of a length of the handle.

12. The XRF analyzer of claim 7, wherein the hand shield has a width that is at least as large as a width of the handle along at least 50% of a length of the hand shield.

13. The XRF analyzer of claim 7, further comprising:
l. a hollow formed in the hand shield; and
m. a digital pulse processor disposed in the hollow and electrically connected to the x-ray detector.

14. The XRF analyzer of claim 7, further comprising:
l. a power component including electrical connections configured for electrical connection to a portable, electric power-source;
m. the handle and the hand shield extending in two separate, parallel columns from the engine component to the power component and attaching the engine component to the power component; and
n. an XRF analyzer housing including two housing portions, each housing portion including an engine component casing section, a power component casing section, a hand shield casing section, and a handle casing section that are integrally formed in a single, monolithic body formed together at the same time by injection molding with a plastic impregnated with an element having an atomic number of at least 42.

15. A portable x-ray fluorescence (XRF) analyzer comprising:
a. an engine component having an x-ray emission end and an engine component casing;
b. an x-ray source and an x-ray detector disposed in and substantially enclosed by the engine component casing;
c. the x-ray source disposed in a location and oriented to emit x-rays outward from the x-ray emission end towards a sample;
d. the x-ray detector disposed in a location and oriented to receive fluoresced x-rays emitted from the sample;
e. an x-ray source heat-sink disposed in an opening in the engine component casing and adjacent a side of the x-ray source;
f. an x-ray detector heat-sink disposed in another opening in the engine component casing and adjacent a side of the x-ray detector;
g. the x-ray source heat-sink separated from the x-ray detector heat sink by a material having a thermal conductivity of less than 10 W/(m*K).

16. The XRF analyzer of claim 15, wherein the material that separates the x-ray source heat-sink from the x-ray detector heat sink is a segment of the engine component casing.

17. The XRF analyzer of claim 15, wherein the x-ray source heat-sink is separated from the x-ray detector heat sink by at least 3 millimeters of the material.

18. The XRF analyzer of claim 15, wherein the x-ray source heat-sink and the x-ray detector heat sink are each secured in place by a flange-portion of the engine component casing with an edge of each heat sink disposed under the flange-portion.

19. The XRF analyzer of claim 15, further comprising a compressible gap pad disposed between and adjoining the x-ray source and the x-ray source heat sink, a compressible gap pad disposed between and adjoining the x-ray detector and the x-ray detector heat sink, each compressible gap pad having a thermal conductivity of at least 0.75 W/(m*K).

20. A method of assembling a portable x-ray fluorescence (XRF) analyzer, the method comprising:
a. injection molding, with a plastic impregnated with an element having an atomic number of at least 42, an XRF analyzer housing in two separate portions:
   i. each portion including an engine component casing section attached to a power component casing section by a handle casing section and a hand shield casing section, and
   ii. wherein the handle casing section and the hand shield casing section extend in two separate, parallel columns between the engine component casing section and the power component casing section; and
b. attaching the two XRF analyzer housing portions to each other and sandwiching between the two engine component casing, sections an x-ray source and an x-ray detector such that:
   i. the x-ray source is disposed in a location to emit x-rays outward from the XRF analyzer towards a sample;
   ii. the x-ray detector is disposed in a location to receive fluoresced x-rays emitted from the sample;
   iii. the two hand shield casing sections form a hand shield;
   iv. the two handle casing sections form a handle; and
   v. the hand shield is disposed closer to an x-ray emission end of the x-ray source than the handle.

21. The method of claim 20, wherein attaching the two XRF analyzer housing portions to each other further comprises:
c. disposing an x-ray source heat sink adjacent the x-ray source in an opening in the housing;
d. disposing an x-ray detector heat sink adjacent the x-ray detector in another opening in the housing; and e. disposing a segment of the housing between the x-ray source heat sink and the x-ray detector heat sink.

\* \* \* \* \*